United States Patent
Blömker et al.

(10) Patent No.: US 8,669,302 B2
(45) Date of Patent: Mar. 11, 2014

(54) COMPOSITE MATERIAL COMPRISING A MONOMER WITH A POLYALICYCLIC STRUCTURE ELEMENT AS A SEALING MATERIAL

(75) Inventors: Tobias Blömker, Cuxhaven (DE); Manfred Stepputtis, Kutenholz (DE); Manfred Thomas Plaumann, Cuxhaven (DE); Reinhard Maletz, Cuxhaven (DE)

(73) Assignee: VOCO GmbH, Cuxhaven (DE)

( * ) Notice: Subject to any disclaimer, the term of this patent is extended or adjusted under 35 U.S.C. 154(b) by 134 days.

(21) Appl. No.: 13/249,053

(22) Filed: Sep. 29, 2011

(65) Prior Publication Data

US 2012/0083550 A1 Apr. 5, 2012

(30) Foreign Application Priority Data

Sep. 30, 2010 (DE) .......................... 10 2010 041 800
Sep. 29, 2011 (EP) ..................................... 11183345

(51) Int. Cl.
*A61K 6/083* (2006.01)
*A61C 5/00* (2006.01)
*C08K 3/22* (2006.01)
*C08K 3/40* (2006.01)

(52) U.S. Cl.
USPC ........ 523/116; 523/118; 523/217; 433/228.1; 977/919

(58) Field of Classification Search
USPC ......... 523/116, 118, 217; 433/228.1; 977/919
See application file for complete search history.

(56) References Cited

U.S. PATENT DOCUMENTS

| | | | |
|---|---|---|---|
| 3,815,239 A | 6/1974 | Lee, Jr. et al. | |
| 4,160,080 A | 7/1979 | Koenig et al. | |
| 4,323,696 A | 4/1982 | Schmitz-Josten et al. | |
| 4,379,695 A * | 4/1983 | Orlowski et al. | 433/217.1 |
| 4,447,520 A | 5/1984 | Henne et al. | |
| 4,772,530 A | 9/1988 | Gottschalk et al. | |
| 4,874,450 A | 10/1989 | Gottschalk | |
| 4,925,982 A | 5/1990 | Urano et al. | |
| 4,954,414 A | 9/1990 | Adair et al. | |
| 5,055,372 A | 10/1991 | Shanklin et al. | |
| 5,057,393 A | 10/1991 | Shanklin et al. | |
| 5,228,907 A * | 7/1993 | Eppinger et al. | 106/35 |
| 5,761,169 A | 6/1998 | Mine et al. | |
| 6,573,312 B2 | 6/2003 | Han et al. | |
| 6,617,413 B1 | 9/2003 | Bruchmann et al. | |
| 6,670,499 B1 | 12/2003 | Inoue et al. | |
| 6,899,948 B2 | 5/2005 | Zhang et al. | |
| 7,081,485 B2 | 7/2006 | Suh et al. | |
| 7,148,382 B2 | 12/2006 | Wolf et al. | |
| 7,264,882 B2 | 9/2007 | Engelbrecht | |
| 7,365,222 B2 | 4/2008 | Moszner et al. | |
| 7,381,785 B2 | 6/2008 | Detrembleur et al. | |
| 7,585,901 B2 | 9/2009 | Moszner et al. | |
| 7,601,767 B2 | 10/2009 | Ruppert et al. | |
| 2005/0288387 A1 | 12/2005 | Feng et al. | |
| 2006/0063853 A1 | 3/2006 | Hurwitz et al. | |
| 2006/0252845 A1 * | 11/2006 | Ruppert et al. | 523/115 |
| 2007/0027229 A1 | 2/2007 | Moszner et al. | |
| 2007/0166450 A1 | 7/2007 | Simonton et al. | |
| 2009/0036565 A1 * | 2/2009 | Utterodt et al. | 523/116 |
| 2009/0047633 A1 | 2/2009 | Huo et al. | |
| 2010/0016464 A1 | 1/2010 | Craig et al. | |

FOREIGN PATENT DOCUMENTS

| | | | |
|---|---|---|---|
| DE | 3338077 A1 | 5/1985 | |
| DE | 3703120 A1 | 1/1988 | |
| DE | 4231579 A1 | 3/1993 | |
| DE | 4416857 C1 | 6/1995 | |
| DE | 19903177 A1 | 7/2002 | |
| DE | 10119831 A1 | 10/2002 | |
| DE | 10352260 B3 | 4/2005 | |
| DE | 102004060285 A1 | 6/2006 | |
| DE | 60116142 T2 | 7/2006 | |
| DE | 102006019092 A1 | 3/2007 | |
| DE | 102006050153 A1 | 5/2008 | |
| DE | 102007040240 A1 | 2/2009 | |
| DE | 102007040239 A1 | 5/2009 | |
| EP | 0057474 A2 | 7/1979 | |
| EP | 0007508 A2 | 2/1980 | |
| EP | 0047902 A2 | 8/1981 | |
| EP | 0049631 A1 | 10/1981 | |
| EP | 0059451 A1 | 2/1982 | |
| EP | 0106176 A1 | 4/1984 | |
| EP | 0173567 A2 | 8/1985 | |
| EP | 0184095 A2 | 11/1985 | |
| EP | 0206074 A2 | 6/1986 | |
| EP | 0209700 A2 | 6/1986 | |
| EP | 0262629 A2 | 9/1987 | |
| EP | 0254185 A1 | 1/1988 | |
| EP | 0325266 A2 | 7/1989 | |
| EP | 0366977 A2 | 10/1989 | |
| EP | 0682012 A1 | 11/1995 | |
| EP | 0712840 A1 | 5/1996 | |
| EP | 0783880 A2 | 7/1997 | |
| EP | 0867457 A1 | 9/1998 | |
| EP | 0948955 A1 | 10/1999 | |
| EP | 0980682 A1 | 2/2000 | |
| EP | 1563821 A1 | 1/2001 | |
| EP | 1238993 A1 | 9/2002 | |
| EP | 1236459 B1 | 11/2005 | |
| EP | 1645582 A1 | 4/2006 | |
| EP | 1854445 B1 | 10/2006 | |
| EP | 1719497 A1 | 11/2006 | |
| EP | 1839640 A2 | 3/2007 | |
| EP | 1112995 B1 | 4/2007 | |
| EP | 2016931 A2 | 1/2009 | |
| EP | 2145613 A1 | 1/2010 | |

(Continued)

*Primary Examiner* — Tae H Yoon
(74) *Attorney, Agent, or Firm* — Duane Morris LLP; J. Rodman Steele, Jr.; Gregory M. Lefkowitz

(57) ABSTRACT

The application of certain (preferably photocurable) composite materials comprising a monomer with a polyalicyclic structure element as a dental sealing material is described herein. A description is also provided of novel polymerizable monomers comprising at least one polyalicyclic structure element and certain ethylenic structure elements, which are particularly suitable for use in a composite material to be applied and their application in a composite material.

23 Claims, No Drawings

(56) References Cited

FOREIGN PATENT DOCUMENTS

| | | |
|---|---|---|
| FR | 2640503 A1 | 12/1989 |
| GB | 1110673 | 4/1968 |
| GB | 1576080 | 10/1980 |
| GB | 2310855 A | 10/1997 |
| WO | 9917716 A2 | 4/1999 |
| WO | 0130307 A1 | 5/2001 |
| WO | 0144873 A1 | 6/2001 |
| WO | 02092021 A1 | 11/2002 |
| WO | 02092023 A1 | 11/2002 |
| WO | 2005084611 A1 | 9/2005 |
| WO | 2005094757 A1 | 10/2005 |
| WO | 2006063891 A1 | 6/2006 |
| WO | 2007028159 A2 | 3/2007 |
| WO | 2009065873 A2 | 5/2009 |

* cited by examiner

COMPOSITE MATERIAL COMPRISING A MONOMER WITH A POLYALICYCLIC STRUCTURE ELEMENT AS A SEALING MATERIAL

CROSS-REFERENCE TO RELATED APPLICATIONS

This application claims priority to German Patent Application No. DE 10 2010 041 800.5 filed Sep. 30, 2010, and European Patent Application No. EP 11 183 345 filed Sep. 29, 2011, the entireties of which are incorporated herein by reference.

FIELD OF THE INVENTION

The present invention relates to certain (preferably photo-curable) composite materials comprising a monomer with a polyalicyclic structure element or the application of these in a therapeutic dental method as a sealing material for sealing of fissures and/or pits and/or carious lesions. In the following novel polymerizable monomers are also described comprising at least one polyalicyclic structure element and certain ethylenic structure elements, which are particularly suitable for use in a dental composite material according to the invention or to be applied according to the invention, and their use in a dental composite material according to the invention or to be applied according to the invention.

BACKGROUND OF THE INVENTION

Sealing of Fissures

Fissure sealing means the filling of sometimes very deep pits, rough furrows and grooves on the surface of teeth with a synthetic material having good flow properties. The often narrow recesses on the chewing surfaces are known as fissures. In children and young people, but also in adults, caries often develop first in the fissures of the chewing surfaces, wherein the occlusal surfaces of the side teeth exhibit the greatest propensity to caries. A very pronounced and jagged relief may also be found on the inside of the front teeth, so that here also an anti-carietic sealing may be advisable. A highly pronounced fissure relief also promotes plaque attachment. Plaque accumulation has also been observed in narrow fissures and steep cusp slopes.

The various types of fissure (for example ampoule-shaped, I-shaped, U-shaped, V-shaped) can harbor food remnants and thus offer an ideal and protected habitat for the bacteria that cause caries, since oral hygiene measures such as brushing the teeth do not reach here. The bristles of toothbrushes are generally too broad in order to be able to clean the bottom of the fissure. The morphology of the fissures therefore makes mechanical cleaning of the pits virtually impossible. If superficial tooth decay should occur in the fissure, then this is highly likely to spread rapidly to the dentin, since the thickness of the enamel in the area of the fissure, in particular the base of the fissure, is as a rule very thin. The high susceptibility of fissures to a case of caries is thus primarily explained by their particular morphology.

It has also been reported that the danger of caries in fissures is significantly greater than for smooth tooth surfaces since in the fissures fluoride prevention cannot be as effective as normal.

Various forms of fissure sealing can be identified:
In preventive fissure sealing narrow, deep fissures are sealed with a suitable fine-flowing material.
When sealing a previously drilled fissure the fissure is expanded minimally with the help of a small drill and if no caries is present the sealing is performed with the material.
If when drilling of the fissure caries is found, then this must be removed. The defect that has resulted from the preparation is initially treated with a composite filling which is then covered with the sealing material.

Sealing the fissures makes the tooth relief flatter, the tooth is easier to clean and the occurrence of caries can thus be prevented. These days fissure sealing is recognized as a tested and recommended, effective preventive measure and is becoming increasingly common practice in everyday dentistry. The rule is that all fissures and pits in danger of caries should be sealed as a precaution. It has been shown that such a course of action leads to a significant reduction in cariogenic microorganisms in the fissure below the sealing.

Sealing of Carious Lesions

While fissure sealants are fluid synthetic materials, which are introduced into the occlusal fissure relief following etching of the enamel, in order following curing to create a mechanical and chemical barrier to bacteria and their cariogenic metabolites and thus to prevent the occurrence or advance of caries, fluid, low-viscosity sealing synthetic materials can also be used for infiltration of initial carious lesions. Initial carious lesions are enamel areas with increased pore volumes. These pores constitute diffusion paths for a progressive dissolution of the enamel structure. For this reason it has been proposed, through infiltration with curable materials to both seal off the diffusion paths and achieve a stabilization of the damaged enamel structure. It has been shown that low viscosity synthetic material compositions penetrate lesions and following curing can prevent further demineralization.

Dimethacrylate-based synthetic materials are used as the standard materials for sealing of fissures, pits and carious lesions, which are either not filled, or compared with filling composites to a lesser extent. These materials demonstrate the most favorable retention behavior. Because of their lower filler loading the sealants flow better, compared to filling composites, in the bottom of the fissure or lesion. However, because of the reduced filler content, they are less resistant to abrasion and less flexurally rigid than filling materials.

The materials are distinguished by way of example according to the way that they are cured, which can take place either by photo- and/or autopolymerization. Thus photocurable fissure sealants as single component materials are, compared with two-component autopolymerizable sealing materials, less susceptible during processing since no bubbles can form during mixing. From a clinical point of view, therefore, these materials are preferred.

A further distinguishing feature is the appearance of the material. Thus there are both transparent and colored products. Transparent preparations are unfilled or have nanoscale filler particles added the size of which is smaller than the wavelength of the visible light. These materials allow the dentist, for example following sealing of the fissure, to detect a possible progression of the caries on the bottom of the fissure. On the other hand, a colored material allows the detection of defects in the sealing during follow-up checks. This would not be possible with transparent sealants.

Many variants of the dental sealing materials are also offered as fluoride releasing materials.

In DE 23 01 067 dental fissure sealants are proposed, which are claimed to have highly improved handling characteristics and an excellent ability to completely fill and seal holes and fissures developing in teeth, wherein their compositions contain as principally curable monomer components glycol dimethacrylates, such as for example ethylene glycol dimethacrylate, diethylene glycol dimethacrylate, etc. The inventors noticed that the use of aromatic dimethacrylates is not suited to sealing of fissures since their viscosity is too high to allow them to flow into the holes and fissures and they do not allow completed sealing and good adherence. Glycol dimethacrylates have been used as so-called "reactive thinning monomers" for many years in dental composite compositions in order to adjust and control the high viscosity of the aromatic dimethacrylates. The compositions disclosed are designed to be two-component and are chemically cured.

It can be expected that compositions, as described in DE 23 01 067, because of their relatively large quantity of reactive thinning monomers will absorb a lot of water. The ether groups —$CH_2$—$CH_2$—O— demonstrate free, unimpeded rotation and form highly flexible molecular chains. The packing of the chains in the polymer is thus not rigid and fixed, but movable. The polymer network is open to the entry of water. As a result it is highly likely that large quantities of water will enter the polymer, expand it further and then irreversibly hydrolytically split and degrade it.

In U.S. Pat. No. 6,573,312 B2 a composition for sealing/filling of fissures and pits is indicated containing a chemically modified Bis-GMA (2,2-bis[4-(2-hydroxy-3-methacryloyloxypropoxy)phenyl)propane). The composition is claimed to achieve improved physical and mechanical characteristics of the polymer and the realization of the polymerization is claimed to take place at higher rates during photocuring.

The modification of the Bis-GMA takes place by successive reaction of the secondary hydroxyl groups of the Bis-GMA with methacryloyl chloride in the presence of an organic amine. In the first synthesis step the dimethacrylate is thus reacted to form a trimethacrylate (Tri-GMA) and in a second step to a tetra-functionalized methacrylate (Tetra-GMA).

The compositions consist of Bis-GMA and Tri-GMA as well as Bis-GMA, Tri-GMA and Tetra-GMA, wherein the compositions also contain fillers, photoinitiators, additives and thinning monomers. As thinning monomers methyl methacrylate and glycol dimethacrylate are proposed.

The particular characteristics of dental compositions, based on Bis-GMA, stem from the ability of the molecule, apart from the linking via the methacrylate groups, to form additional structure units, so-called superstructures or secondary/tertiary structure units via hydrogen bonds, based on the free hydroxyl groups. The development of these superstructures can likewise be promoted by carbamate, amide or similarly composed groups, but not by ester groups. Furthermore, as a result of the rigid conformation of the bisphenol-A structural motif the polymer has close, densely packed molecular associations interacting via a number of types of bonds. These structural conditions are behind the good mechanical and physical characteristics of Bis-GMA polymers.

Were these additional interactions to be blocked by functionalization of the free hydroxyl groups, then the formation of the superstructures would be impeded resulting in a drop in the physical and mechanical properties of the cured compositions.

In addition, the properties stated in U.S. Pat. No. 6,573,312 B2 for the physical characteristics are merely assumptions. Differences between the properties of the comparative examples and those of the examples according to the invention from U.S. Pat. No. 6,573,312 B2 are not apparent.

US 2005/0288387 A1 describes dental compositions which is claimed are used for coating of teeth or as dental sealing materials. The compositions contain a multiacrylate compound, an initiator and an alcohol. The multiacrylate compound contains at least 3 acrylate units per molecule, for example dipentaerythritol pentaacrylate, di-trimethylolpropane tetraacrylate, trimethylolpropane triacrylate, etc. The initiator is preferably a photoinitiator.

US 2009/0047633 A1 likewise relates to a dental sealing and/or coating system which adheres to the tooth structure itself. The composition contains 10 through 60 wt. % of a polymerizable compound, comprising Bis-GMA and urethane compounds and mixtures of these, 1 through 40 wt. % of a polymerizable acid compound, 3 through 60 wt. % of a silica filler with an average particle size of 1 through 100 nm, 1 through 30 wt. % water and 10 through 60 wt. % solvent.

EP 0 969 789 B1 describes dental sealing and coating materials which comprise at least 10 wt. % of a polymerizable material, 0.01 through 20 wt. % of a filler in the nano range, having a primary particle size of between 1 and 100 nm, whereby the surface of the filler in the nano range is modified by a chemical surface treatment with a silanizing agent and at least 10 wt. % of an organic solvent with a boiling point below that of water.

U.S. Pat. No. 6,899,948 B2 is also aimed at dental sealing materials, containing in addition to curable monomers, non-aggregated, surface-modified silica particles with an average particle size of less than 200 nm.

WO 2007/028159 A2 relates to clear, transparent and opaque dental sealing compositions, in which colloidal silica particles with an average particle size of 10 through 100 nm are dispersed in methacrylate (acrylate) resin. The compositions can be cured photochemically and are claimed to provide hard, smooth and shiny coatings on the tooth. The non-agglomerated silica particles are claimed to be distributed evenly within the resin matrix so that the dispersion has a low viscosity. The polymers are claimed to have good mechanical properties such as abrasion resistance. The compositions for sealing of fissures and pits are preferably used on the surface of a tooth or a restoration.

In WO 01/30307 A1, inter alia, dental compositions with a visible opacity at a value of less than 0.25 are also indicated. Since the reciprocal characteristic of translucence is opacity, a composition is described here with translucence values that are not less than 0.75. These compositions, which can also be used as a sealing material, are likewise claimed to be transparent. Apart from a curable enamel composition, they have silica particles with an average diameter of less than 200 nm.

A temporary, transparent, dental lacquer composition for coating of tooth surfaces is described in US 2006/0063853 A1. Here the transparency is brought about by the addition of hollow glass balls, wherein the hollow glass balls divert any incoming light back to the light source. This effect is brought about by a total reflection that occurs inside the balls, which always takes place if light enters a hollow glass ball. This phenomenon is used in particular in road markings. In order to be able to create this effect, the refractive index of the binding agent must be less than that of the hollow glass balls.

Both US 2007/0166450 A1 and US 2010/0016464 A1 describe dental coating and sealing materials containing fluorescers.

WO 2005/094757 A1 claims a dental composition which is suitable for use as a fissure and pit sealer and heat-curable polymerization system that is subject to stepwise polymerization. The system can for example be an epoxide/amine, an epoxide/thiol, an epoxide/carboxylic acid, an epoxide/phenol, an isocyanate/amine, an isocyanate/alcohol, an isocyanate/thiol, an isothiocyanate/amine, an isothiocyanate/alcohol, an isothiocyanate/thiol, a blocked isocyanate, a siloxane system or a similar curable system.

EP 1 307 173 B1 describes a fluoride lacquer and silicon-based fissure sealing material.

Published documents DE 20 2006 020 483 U1, DE 20 2006 020 480 U1, DE 20 2006 020 479 U1, DE 20 2006 020 477 U1, DE 20 2006 020 476 U1, EP 2 023 884 A1, EP 1 854 445 A1, EP 2 145 613 A1 and EP 2 151 229 A2 relate to compositions for infiltration of tooth enamel in the treatment or prevention of carious lesions.

(Meth)acrylic acid esters of bis(hydroxymethyl)tricyclo[5.2.1.0$^{2,6}$]decane are known as monomer building blocks for the preparation of sealing masses for tooth enamel fissures. In DE 28 16 823 C2 the ester is used without comonomers and without fillers for such an application. According to this published document compositions of the ester for tooth filling materials were mixed with the comonomers Bis-GMA and hexane diol dimethacrylate.

EP 0 254 185 A1 relates to urethane groups containing (meth)acrylic acid esters of tricyclo[5.2.1.0$^{2,6}$]decanes and their use as dental materials.

DE 10 2007 034 457 (corresponding to EP 2 016 931 A2) describes formulations with a mixture of monomers comprising Bis-GMA and TCD-di-HEMA (bis(methacrylolyoxymethyl)-tricyclo[5.2.1.0$^{2,6}$]decane) or TCD-di-HEA (bis(acrylolyoxymethyl)tricyclo[5.2.1.0$^{2,6}$]decane) with various crosslinkers. The formulations that these contain relate exclusively to dental composite materials for use as filler materials. The same applies to DE 10 2005 021 332 and the corresponding U.S. Pat. No. 7,601,767 B2, DE 35 22 005 A1 discloses (meth)acrylic acid derivatives of tricyclodecanes and their application in dentistry. The same applies for DE 35 22 006 A1.

DE 35 22 005 discloses (meth)acrylic acid derivatives of tricyclodecanes and their application in dentistry. The same applies for DE 35 22 006 A1.

U.S. Pat. No. 6,617,413 B1 discloses compounds which comprise polymerizable double bonds and further functional groups.

The requirements to be met by sealing materials for sealing fissures, pits and carious lesions are extremely varied. Firstly, the compositions must remain on the surface of the tooth for a long time in order to protect the tooth enamel from contamination by bacterial metabolites. In the best case, the material should remain on the enamel for as long as the tooth remains in the mouth of the patient. Such extreme requirements are hardly likely to be met, however. It should nevertheless remain in the tooth surface up until the period during which the greatest caries activity is noted. This is between the ages of 17 and 18 years.

In order to achieve the most long-lasting possible seals, materials that are as abrasion-resistant as possible and that can withstand chewing pressures are necessary. Products with the highest possible filler content have better abrasion resistance. In the sometimes narrow and fine fissures, however, these can no longer be applied or only with great difficulty. A compromise must therefore be found between the greatest possible filler loading on the one hand and a very flowable material with the lowest possible viscosity on the other.

A further, quite important characteristic of sealing materials for sealing of fissures, pits and carious lesions, should be the lowest possible absorption of water by the preparation. During radical cross-linking of methacrylate/acrylate compositions a three-dimensionally linked network results. Because of the very low size of the water molecule water can diffuse into the mesh of the polymer, where it accumulates at certain points in the network and there forms hydrogen bonds or other weak polar bonds. The more polar components that are present in the polymer matrix, the easier it is for further water absorption to take place. As a result of water absorption the polymer expands and an increase in the intermolecular distances take place. This hygroscopic expansion can lead to a structural reorganization of the polymer chains. The resultant compressive stress on the floor of the pit and/or fissures can then cause lasting damage to the tooth enamel. The water absorption takes place over a long period following curing, so that when there is excessive water absorption an expansion stress occurs and thus an "overflowing" of the material. On top of this water molecules can attack sensitive structure elements of the polymer such as for example ester groups, hydrolytically splitting these. This deterioration can lead to complete disintegration of the network and thus to a loss of the product.

On the other hand, a certain polarity of the sealing materials is also desirable, however, since the tooth structure is hydrophilic and polar compositions guarantee a good adaptation and wettability of the material to the tooth substrate.

DESCRIPTION OF THE INVENTION

The object for the invention was to find a dental material which is suitable for sealing of fissures, pits and carious lesions, which is characterized by very low water absorption, very good surface affinity to the tooth structure and exceptional mechanical properties.

In particular, the material to be found should preferably simultaneously
- in the cured state have a water absorption that is less than 25 μg/mm$^3$,
- have a good surface affinity for a contact angle with the dry tooth enamel of less than 60° and
- in the cured state have a flexural strength of more than 105 MPa.

The values for the characteristics given here for the material to be found must be measured under test conditions, as indicated in the following under "Measurement Methods".

Further objects arise from the following description and the attached claims.

The primary object is achieved by a composite material composed of or comprising
(a) as the filler component a total quantity of fillers in the range 0.5 through 60 wt. %, in relation to the total weight of the composite material wherein the total quantity of fillers is a mixture of fillers comprising
  (a1) a total quantity in the range 0.5 through 60 wt. % of non-agglomerated, organically surface-modified nanoparticles with an average particle size of less than 200 nm (preferably less than 60 nm)
  and
  (a2) a total quantity in the range 0 through 59.5 wt. % of microparticles with an average particle size in the range 0.4 μm through 10 μm,
  and
  (a3) optionally additional fillers,
  wherein the weight percentages given for components (a1) and (a2) in each case relate to the total weight of the composite material,
(b) as the monomer component a total quantity of polymerizable monomers in the range 24 (preferably 39) through 98.5 wt. %, in relation to the total weight of the composite material, wherein the total quantity of polymerizable monomers comprises
  (b1) one, two or a plurality of monomers selected from the group consisting of compounds (monomers) with the structure Q(Y$_x$Z$_e$)$_b$, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups (here preferably C1-C4-alkyl), alkoxy groups (here preferably C1-C4-alkoxy), halogen atoms (here preferably F) or trifluormethyl groups, b is an integer selected from the group of integers 1, 2, 3 and 4, each Z represents a structure element, which independently of any other structure elements Z is selected from the group consisting of

—O—(C=O)—CH=CH$_2$, —O—(C=O)—C(CH$_3$)=CH$_2$,

—(C=O)—CH=CH$_2$, —(C=O)—C(CH$_3$)=CH$_2$

—CH=CH$_2$, —C(CH$_3$)=CH$_2$ and —O—CH=CH$_2$, each index e is an integer, which independently of any other indices e is selected from the group of integers 1, 2, 3 and 4, each index x independently of any other indices x represents 0 or 1, each Y in the structure $Q(Y_xZ_e)_b$ where x=1 represents a structure element, which binds the polyalicyclic structure element Q with e structure elements Z, wherein each Y is selected independently of any other structure elements Y, (b2) optionally one, two or a plurality of further radically polymerizable monomers from the group consisting of acrylates and methacrylates, preferably from the group of methacrylates, wherein the further radically polymerizable monomer(s) are not compounds (monomers) of the structure $Q(Y_xZ_e)_b$ defined above, (c) one or a plurality of initiators and/or catalysts, preferably in a quantity of up to 1 wt. %, in relation to the total weight of the composite material,
and (d) optionally one or a plurality of additives for application in a therapeutic dental method as a sealing material for sealing of fissures and/or pits and/or carious lesions.

In other words, the problem is solved by a composite material consisting of or comprising (a) as the filler component a total quantity of fillers in the range 0.5 through 60 wt. %, in relation to the total weight of the composite material wherein the total quantity of fillers is a mixture of fillers comprising (a1) a total quantity in the range 0.5 through 60 wt. % of non-agglomerated, organically surface-modified nanoparticles with an average particle size of less than 200 nm
and (a2) a total quantity in the range 0 through 59.5 wt. % of microparticles with an average particle size in the range 0.4 μm through 10 μm,
and (a3) optionally further fillers, wherein the weight percentages given for components (a1) and (a2) in each case relate to the total weight of the composite material, (b) as the monomer component a total quantity of polymerizable monomers in the range 24 (preferably 39) through 98.5 wt. %, in relation to the total weight of the composite material, wherein the total quantity of polymerizable monomers comprises (b1) one, two or a plurality of monomers selected from the group consisting of compounds (monomers) with the structure $Q(YZ_e)_b$, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups, b is an integer selected from the group of integers 1, 2, 3 and 4, each Z represents a structure element, which independently of any other structure elements Z is selected from the group consisting of

—O—(C=O)—CH=CH$_2$, —O—(C=O)—C(CH$_3$)=CH$_2$,

—(C=O)—CH=CH$_2$, —(C=O)—C(CH$_3$)=CH$_2$

—CH=CH$_2$, —C(CH$_3$)=CH$_2$ and —O—CH=CH$_2$, each index e is an integer, which independently of any other indices e is selected from the group of integers 1, 2, 3 and 4, each Y represents a structure element, which in the structure $Q(YZ_e)_b$ binds the polyalicyclic structure element Q with e structure elements Z, wherein each Y is selected independently of any other structure elements Y or is omitted, (b2) optionally one, two or a plurality of further radically polymerizable monomers from the group consisting of acrylates and methacrylates, preferably from the group of methacrylates, wherein the further radically polymerizable monomer(s) are not compounds (monomers) of the structure $Q(YZ_e)_b$ defined above, (c) one or a plurality of initiators and/or catalysts, preferably in a quantity of up to 1 wt. %, in relation to the total weight of the composite material,
and (d) optionally one or a plurality of additives for application in a therapeutic dental method as a sealing material for sealing of fissures and/or pits and/or carious lesions.

All the statements below relating to the compounds of structure $Q(YZ_e)_b$ (wherein each Y is selected independently of any other structure elements Y or is omitted) and the preferred or particularly preferred configurations of the present invention indicated in connection with these compounds apply accordingly to the compounds of structure $Q(Y_xZ_e)_b$ (wherein each index x independently of any other indices x represents 0 or 1), and vice versa.

Such a compound of structure $Q(Y_xZ_e)_b$ comprises a polyalicyclic structure element Q, which is derived from a corresponding polyalicyclic hydrocarbon. In the context of the present text, this means that b hydrogen atoms of the hydrocarbon are replaced by substituents $Y_xZ_e$ (as described above), and optionally one, two or a plurality of the hydrogen atoms not substituted by $Y_xZ_e$ are substituted by alkyl groups, alkoxy groups, halogen atoms or trifluormethyl groups. The polyalicyclic structure element Q is constituted by carbon ring atoms. Carbon atoms outside the rings are a component of substituents.

Within the context of the present text (meth)acrylic means both acrylic and methacrylic.

The "polyalicyclic" structure element Q is a bicyclic, tricyclic, tetracyclic, pentacyclic or hexacyclic hydrocarbon radical as defined above. The designations "bicyclic", "tricyclic", "tetracyclic", "pentacyclic" and "hexacyclic" here correspond to the IUPAC nomenclature.

In other words Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element Q not substituted by substituents $Y_xZ_e$ is or are substituted by alkyl groups (here preferably C1-C4-alkyl), alkoxy groups (here preferably C1-C4-alkoxy), halogen atoms (here preferably F) or trifluormethyl groups.

Preferably each Y represents a structure element, which in the structure $Q(Y_xZ_e)_b$ with x=1, binds the polyalicyclic structure element Q with e structure elements Z, wherein each Y is selected independently of any other structure elements Y.

The composite materials to be used or applied according to the invention, preferably in one of the configurations identified in the following as preferred or particularly preferred, are in particular suitable for sealing of fissures, sealing of pits and sealing of carious lesions.

In a further aspect the invention therefore relates to a composite material, preferably in one of the configurations identified in the following as preferred or particularly preferred, as or for use or application as a dental sealing material, preferably as a sealing material for sealing of fissures, for sealing of pits or for sealing of carious lesions.

It has been found that the composite materials to be applied according to the invention for the stated purposes are very good dental sealing materials, which compared with a sealing material from the prior art on the dried tooth enamel demonstrate a much better surface affinity (in particular in respect of the contact angle with the dry tooth enamel), absorb very much less water and have good mechanical properties (in particular flexural strength and modulus of elasticity).

The composite material to be used or applied according to the invention is preferably photocurable.

The total of the numerical values of the index b and the index e is preferably 3, 4, 5, 6, 7 or 8.

In the uncured state a composite material to be used or applied according to the invention, is characterized by a low contact angle to the dry tooth enamel (preferably of less than 60°, preferably less than 50°, particularly preferably less than 40°, and particularly preferably less than 35°, measured with a contact angle measuring instrument from Krüss (DSA 100).

It has further become apparent that a composite material to be used or applied according to the invention, in the cured state has a very low water absorption, preferably less than 15 µg/mm$^3$, preferably less than 13 µg/mm$^3$ and particularly preferrably less than 10 µg/mm$^3$. Here the water absorption was determined analogous to ISO 4049.

Preference is for a composite material to be used or applied according to the invention, wherein the filler component (a) comprises (a1) a total quantity in the range 0.5 through 59.5 wt. % of non-agglomerated, organically surface-modified nanoparticles with an average particle size of less than 60 nm and/or (a2) a total quantity in the range 0.5 through 59.5 wt. % of microparticles with an average particle size in the range 0.4 µm through 10 µm, and (a3) optionally additional fillers, wherein the weight percentages given for components (a1) and (a2) in each case relate to the total weight of the composite material.

Preference is for a composite material to be used or applied according to the invention, wherein the filler component (a) (a3) comprises a total quantity in the range 0 through 15 wt. %, preferably 0 through 10 wt. %, of additional (further) fillers, wherein the weight percentage given for component (a3) relates to the total weight of the composite material.

Preference is for a composite material to be used or applied according to the invention, wherein the monomer component (b) contains (b1) one, two or a plurality of radically polymerizable monomers of structure $Q(Y_xZ_e)_b$ as defined above and (b2) one, two or a plurality of additional radically polymerizable monomers from the group consisting of acrylates and methacrylates, preferably from the group of methacrylates, wherein the further radically polymerizable monomer(s) are not compounds (monomers) of the structure $Q(Y_xZ_e)_b$ as defined above, wherein the ratio of the total weight of component (b1) to the total weight of component (b2) is preferably in the range 4:1 through 1:3, preferably in the range 3:1 through 1:2.

Similarly preferred is a composite material to be used or applied according to the invention, comprising or consisting of (a) as the filler component a total quantity of fillers in the range 0.5 through 60 wt. %, in relation to the total weight of the composite material wherein the total quantity of fillers is a mixture of fillers comprising (a1) a total quantity in the range 0.5 through 60 wt. % of non-agglomerated, organically surface-modified nanoparticles with an average particle size of less than 200 nm (preferably less than 60 nm)

and (a2) a total quantity in the range 0 through 59.5 wt. % of microparticles with an average particle size in the range 0.4 µm through 10 µm, and (a3) optionally additional fillers, wherein the weight percentages given for components (a1) and (a2) in each case relate to the total weight of the composite material, (b) as the monomer component a total quantity of polymerizable monomers in the range 24 (preferably 39) through 89 wt. %, preferably 35 (particularly preferably 44) through 60 wt. %, in relation to the total weight of the composite material, wherein the total quantity of polymerizable monomers comprises (b1) one, two or a plurality of monomers selected from the group consisting of compounds (monomers) with the structure $Q(Y_xZ_e)_b$, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups (here preferably C1-C4-alkyl), alkoxy groups (here preferably C1-C4-alkoxy), halogen atoms (here preferably F) or trifluormethyl groups, b is an integer selected from the group of integers 1, 2, 3 and 4, each Z represents a structure element, which independently of any other structure elements Z is selected from the group consisting of

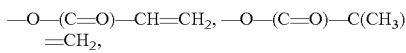

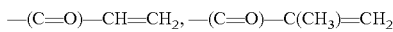

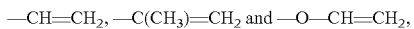

each index e is an integer, which independently of any other indices e is selected from the group of integers 1, 2, 3 and 4, each index x independently of any other indices x represents 0 or 1, each Y in the structure $Q(Y_xZ_e)_b$ where x=1 represents a structure element, which binds the polyalicyclic structure element Q with e structure elements Z, wherein each Y is selected independently of any other structure elements Y, (b2) one, two or a plurality of further radically polymerizable monomers from the group consisting of acrylates and methacrylates, preferably from the group of methacrylates, wherein the further radically polymerizable monomer(s) are not compounds (monomers) of the structure $Q(Y_xZ_e)_b$ defined above, wherein the ratio of the total weight of component (b1) to the total weight of component (b2) is in the range 4:1 through 1:3, preferably in the range 3:1 through 1:2, (c) one or a plurality of initiators and/or catalysts, preferably in a quantity of up to 1 wt. %, in relation to the total weight of the composite material, and (d) optionally one or a plurality of additives for application in a therapeutic dental method as a sealing material for sealing of fissures and/or pits and/or carious lesions.

Composite materials to be used or applied according to the invention are in particular designed so that they can be used as a dental material, in particular for sealing of fissures, for sealing of pits and for sealing of carious lesions. Corresponding uses or applications of a composite material according to or to be used (applied) according to the invention are preferred.

The composite material to be used or applied according to the invention comprises or consists of various components for which the following applies:

Component (a): Filler Component

A composite material to be used or applied according to the invention contains a total quantity of fillers, wherein this total quantity is a mixture of fillers comprising (a1) a total quantity in the range 0.5 through 60 wt. % of non-agglomerated, organically surface-modified nanoparticles with an average particle size of less than 200 nm and (a2) a total quantity in the range 0 through 59.5 wt. % of microparticles with an average particle size in the range 0.4 μm through 10 μm, and (a3) optionally further fillers.

In preferred configurations according to the invention a composite material to be used or applied according to the invention contains an amount of filler component (a) in the range 1 through 60 wt. %, preferably 25 through 60 wt. %, more preferably in the range 30 through 60 wt. %, particularly preferably in the range 40 through 60 wt. %.

The average particle size $d_{50}$ of the filler particles to be used or applied according to the invention of the filler component (a) of a composite material according to the invention or to be applied according to the invention is determined by means of light scattering (laser diffraction), for example with a Beckman Coulter LS 13320 particle size analyzer.

Filler component (a) comprises a filler (a1) in the form of non-agglomerated, organically surface-modified nanoparticles with an average particle size of less than 200 nm.

Filler component (a) can in additionally comprise a filler (a2) that differs from component (a1) in the form of microparticles with an average particle size in the range 0.4 μm through 10 μm.

The filler component (a) can furthermore comprise additional further fillers as component (a3), but must not comprise any further filler. The amount of component (a3) is preferably a maximum of 15 wt. %, preferably a maximum of 10 wt. %, more preferably less than 5 wt. %, in each case in relation to the total weight of the composite material.

Filler component (a) comprises in a preferred configuration a mixture of a first filler (a1) in the form of non-agglomerated, organically surface-modified nanoparticles with an average particle size of less than 200 nm and a second filler (a2) in the form of microparticles with an average particle size in the range 0.4 μm through 10 μm.

Through the combination of (a1) nanoparticles and (a2) microparticles in a preferred composite material according to the invention complete and even volumetric filling of the composite material is achieved. In this way both the shrinkage of the composite material as the polymer matrix cures and the sensitivity of the composite material to abrasion are reduced.

A preferred filler component (a) of a composite material to be used or applied according to the invention consists of or comprises:

(a1) a total quantity in the range 10 through 60 wt. % of non-agglomerated, organically surface-modified nanoparticles with an average particles size of less than 200 nm, preferably a total quantity in the range 0.5 through 59.5 wt. % of non-agglomerated, organically surface-modified nanoparticles with an average particle size of less than 60 nm and/or (preferably and)

(a2) a total quantity in the range 0.5 through 59.5 wt. % of microparticles with an average particle size in the range 0.4 μm through 10 μm, preferably a total quantity in the range 20 through 59.5 wt. % of microparticles with an average particle size of 0.4 μm through 10 μm and preferably (a3) a total quantity in the range 0 through 15 wt. % of additional fillers, wherein the weight percentages given for components (a1), (a2) and (a3) relate to the total weight of the composite material.

Further preferred filler components (a) consist of:

(a1) a total quantity in the range 20 through 60 wt. %, preferably 30 through 55 wt. %, of non-agglomerated, organically surface-modified nanoparticles with an average particle size of less than 200 nm and/or (preferably and)

(a2) a total quantity in the range 25 through 59.5 wt. %, preferably 30 through 55 wt. %, of microparticles with an average particle size in the range 0.4 μm through 10 μm, and (a3) a total quantity in the range 0 through 10 wt. %, preferably 0 through 5 wt. %, preferably 1 through 4 wt. % of additional fillers, wherein the weight percentages given for components (a1), (a2) and (a3) relate to the total weight of the composite material.

In a composite material to be used or applied according to the invention containing microparticles of component (a2) the filler quantity can be increased even further whilst still retaining the exceptional surface affinity and flow characteristics by the addition of one or a plurality of nanoscale fillers (a1), allowing the mechanical characteristics of the composite material to be used or applied according to the invention to be further improved.

This applies in particular to composite materials in which component (a2) contains or consists of one or a plurality of glass ceramics.

Component (a1): Non-Agglomerated, Organically Surface-Modified Nanoparticles

Within a composite material to be used or applied according to the invention the function of the nanoparticles is, inter alia, to improve the sealing (e.g. of fissures and pits), and to increase the hardness and abrasion resistance.

Where a composite material to be used or applied according to the invention also contains microparticles of component (a2), the nanoparticles can fill the spaces between the microparticles in order in this way to bring about an even filling by the composite material.

In connection with the present invention, nanoparticles mean particles with an average particle size of less than 200 nm. Preferably the average particle size is less than 100 nm and particularly preferably less than 60 nm.

The amount of organically surface-modified nanoparticles with an average particle size of less than 200 nm is preferably greater than 10 wt. % (e.g. >10 wt. %), preferably greater than 20 wt. % and particularly preferably greater than 25 wt. %.

In transparent composite materials to be used or applied according to the invention the amount of component (a1) is preferably greater than 30 wt. %, preferably greater than 35 wt. % and particularly preferably greater than 40 wt. %.

Our own research has shown that where the content of non-agglomerated, organically surface-modified nanoparticles with a particle size of less than 200 nm is 10 wt. % or less, the composite material is in individual cases no longer abrasion-resistant. On the other hand, it has been shown that where the content of non-agglomerated, organically surface-modified nanoparticles with an average particle size of less than 200 nm is more than 60 wt. %, the processability of the composite material is no longer sufficient; because of the high filler content its static viscosity is then too high, i.e. the material is gel-like in the resting state.

In a preferred configuration a composite material to be applied according to the invention has a viscosity of 100 Pas or less, preferably 50 Pas or less, particularly preferably 10 Pas or less, determined under test conditions, as indicated in the following under "Measurement Methods" (in summary: 23° C., 10 rad/s, 25 mm plate-plate system).

In a preferred configuration a composite material to be used or applied according to the invention comprises a large amount of nanoparticles of component (a1), preferably in a quantity of more than 25 wt. %, preferably in the range 30 through 60 wt. %, particularly preferably in the range 35 through 55 wt. %, in each case in relation to the total weight of the composite material. Such a preferred composite material to be used or applied according to the invention, in particular a preferred dental composite material to be used or applied according to the invention, is characterized by a low abrasion (preferably less than 100 µm, preferably less than 80 µm, more preferably less than 70 µm, determined according to the ACTA method).

The materials for the nanoparticles to be used according to the invention are preferably oxides or mixed oxides and preferably selected from the group consisting of oxides and mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof. Here, as explained, the preferred oxidic nanoparticles are not agglomerated.

In a preferred configuration the nanoscale particles are present in non-agglomerated form, for example dispersed in a medium, preferably in monodisperse form.

In order to allow the nanoparticles to bind properly in the polymer matrix of a composite material to be used or applied according to the invention, the surfaces of the nanoparticles (preferably the preferred oxidic nanoparticles) are organically modified, i.e. their surfaces have organic structure elements. One example of surface treatment of the fillers is the use of a silane. Methacryloxypropyltrimethoxysilane is particularly well-suited as a binding agent.

If for the filler component (a) exclusively a nanoscale filler (a1) is used, then transparent sealing materials can be obtained (see WO 01/30307 A1 and WO 2007/028159 A2). Very good abrasion properties are then achieved. The transparent dental composite materials to be used or applied according to the invention, compared to the products from the prior art, are characterized by a highly improved surface affinity to the tooth enamel, in particular the dry tooth enamel, and by much lower water absorption.

Therefore in a preferred embodiment the filler mixture (a) of a composite material to be used or applied according to the invention comprises exclusively (a1) non-agglomerated, organically surface-modified nanoparticles with an average particle size of less than 200 nm.

Component (a2): Microparticles with an Average Particle Size in the Range 0.4 µm Through 10 µm Within a composite material to be used or applied according to the invention microparticles of component (a2) can bring about an extensively even filling of the volume, wherein the remaining cavities between the microparticles are preferably, and at least to some extent, filled by the nanoparticles described above (component (a1).

In connection with the present invention, microparticles mean particles with an average particle size of 400 nm through 10 µm. Preferably, the average particle size is less than 5 µm. Our own research has shown that the volumetric filling of the composite material that can already be achieved with the microparticles is more complete and even the smaller the microparticles are.

The microparticles of component (a2) can have a monomodal or polymodal, for example a bimodal, particle size distribution. Microparticles with a bimodal or multimodal particle size distribution are preferred according to the invention, since with these a more complete volumetric filling can be achieved than with the general use of microparticles with monomodal particle size distribution. In the case of a bi- or multimodal particle size distribution the particles from the fractions with the larger particle sizes bring about a coarse filling of the volume, while the particles from the fraction with the smaller particle sizes where possible fill the cavities between the particles from the fractions with the larger particle sizes.

Preferably, therefore, in a composite material to be used or applied according to the invention a component (a2) will be used which contains two or a plurality of fractions of microparticles wherein the average particle sizes of the fractions differ from one another.

Preferably component (a2) contains at least two microparticle fractions, wherein the average particles sizes of these differ from one another by at least 0.5 µm, preferably by at least 0.7 µm and more preferably by at least 1 µm.

The microparticles of various fractions can consist of the same or different materials; here several fractions of microparticles can be present, the average particle sizes of which are approximately the same or are within a certain range, wherein the particle materials differ between the fractions.

A composite material to be used or applied according to the invention preferably comprises a component (a2), having one or a plurality of first microparticle fractions, which in each case have an average particle size in the range 1 µm through 10 µm, preferably 1 µm through 5 µm, and one or a plurality of second microparticle fractions, which in each case have an average particle size in the range >0.4 µm through <1 µm (e.g. larger than 0.4 µm, but smaller than 1 µm), preferably 0.5 µm through 0.8 µm.

The ratio of the total weight of the first microparticle fractions to the total weight of the second microparticle fractions is preferably in the range 1:3 through 1:15, preferably in the range 1:8 through 1:13.

The ratio of the average grain size of the or a first microparticle fraction to the average grain size of the or a second microparticle fraction of component (a2) is preferably in the range 1.5:1 through 12:1, preferably in the range 2:1 through 7:1.

In an particularly preferred composite material to be used or applied according to the invention the component (a2) comprises one or a plurality of first microparticle fractions, which in each case have an average particle size in the range 1 µm through 10 µm, preferably 1 µm through 5 µm, and one or a plurality of second microparticle fractions, which in each case have an average particle size in the range >0.4 µm through <1 µm, preferably 0.5 µm through 0.8 µm, wherein the ratio of the total weight of the first microparticle fractions to the total weight of the second microparticle fractions is in the range 1:3 through 1:15, preferably in the range 1:8 through 1:13 and/or the ratio of the average grain size of the or a first microparticle fraction to the average grain size of the or a second microparticle fraction of component (a2) is in the range 1.5:1 through 12:1, preferably 2:1 through 7:1.

The base materials for the microparticles to be used according to the invention in surface-modified form are preferably selected from the group consisting of quartz glass ceramic or glass powder (particularly dental glass powder), barium or strontium glasses, fluoride ion-emitting glasses, oxides of aluminum or silicon, zeolites, apatite, zirconium silicates, hardly soluble metal salts such as barium sulfate or calcium fluoride and radiopaque fillers such as ytterbium fluoride.

For improved bonding in the polymer matrix of a composite material to be used or applied according to the invention the microparticles are preferably organically surface-modified. One example of surface treatment of the fillers is the use of a silane, leading to silanized microparticles. Methacryloxypropyltrimethoxysilane is particularly well-suited for surface treatment (as a binding agent).

In an particularly preferred composite material to be used according to the invention at least part of the microparticles of component (a2) is made up of organically surface-modified particles, preferably silanized particles and/or at least part of the microparticles of component (a2) is made up of dental glass particles; preferably at least part of the microparticles of component (a2) is organically surface-modified dental glass particles, preferably silanized dental glass particles.

Preferably in these cases component (a2) is characterized by a bi- or multi-modal particle size distribution, in particular a bi- or multi-modal particle size distribution with the preferred features described above.

Component (a3)-Additional (Further) Fillers

The filler component (a) can further comprise an additional filler (a3). This filler (a3) comprises no non-agglomerated, organically surface-modified nanoparticles with an average particles size of less than 200 nm (which must be attributed to component (a1) and also comprises no microparticles with an average particle size of 0.4 µm through 10 µm (which must be attributed to component (a2)). The filler component (a) preferably comprises in addition to components (a1) and/or (a2) additional further fillers as component (a3).

Thus, for example, filler materials with a strengthening effect such as glass fibers, polyamide or carbon fibers can be used. A composite material to be used or applied according to the invention can also contain fine particle splinters or bead polymers, wherein the bead polymers can be homo- or copolymers of organically curable monomers.

Component (b): Monomer Component

Within a composite material to be used or applied according to the invention the function of the monomer component (b) is to form a matrix in which the abovementioned fillers (a) are integrated. This matrix is formed by polymerization, particularly radical polymerization, of (b1) one, two or a plurality of monomers of structure $Q(Y_xZ_e)_b$, optionally together with component (b2) one, two or a plurality of further radically polymerizable monomers from the group consisting of acrylates and methacrylates, wherein the further radically polymerizable monomer(s) is or are not compounds (monomers) of structure $Q(Y_xZ_e)_b$ as defined above.

Preferably the monomer component (b) is a mixture of monomers consisting of or comprising both component (b1) and component (b2).

Preferred composite materials to be used or applied according to the invention comprise monomer component (b) in a quantity in the range 24 (preferably 39) through 89 wt. %, preferably 30 (preferably 42) through 65 wt. %, preferably in the range 35 (preferably 44) through 60 wt. %, in relation to the total weight of the composite material.

Particularly good results in terms of the present invention are achieved if the weight ratio of the total quantity of monomer component (b1) to the total quantity of monomer component (b2) is in the range 4:1 through 1:3, preferably in the range 3:1 through 1:2, preferably in the range 2:1 through 2:3, particularly preferably in the range 3:2 through 2:3, and quite particularly preferably in the range 4:3 through 3:4.

This preferably applies to monomers of component (b1), in which the polyalicyclic structure element Q represents a tricyclo[$5.2.1.0^{2,6}$]decane radical, in particular to monomers of the component (b1), which are reaction products of the bis (hydroxymethyl)tricyclo[$5.2.1.0^{2,6}$]decane.

Here the polyalicyclic structure element Q of component (b1) ensures a sterically rigid and hydrophobic spine, and the other monomers of component (b2) ensure sufficient cross-linking, in particular with the surface-modified fillers. Our own investigations have shown that pastes with a lower amount of component (b2) or without component (b2) have increased abrasion, whereas pastes with a lower amount of component (b1) or without component (b1) demonstrate increased water absorption and less favorable mechanical characteristics (in particular a lower modulus of elasticity).

Component (b1): One, Two or a Plurality of Monomers of Structure $Q(Y_xZ_e)_b$ with at Least One Polyalicyclic Structure Element Component (b1) is comprised one, two or a plurality of monomers of structure $Q(Y_xZ_e)_b$ defined above, wherein Z preferably represents a structure element that independently of any other structure elements Z is selected from the group consisting of —O—(C=O)—CH=CH$_2$, —O—(C=O)—C(CH$_3$)=CH$_2$, —(C=O)—CH=CH$_2$ or —(C=O)—C(CH$_3$)=CH$_2$. Preference is for compounds of structure $Q(Y_xZ_e)_b$, wherein Z is selected from the group consisting of —O—(C=O)—CH=CH$_2$, —O—(C=O)—C(CH$_3$)=CH$_2$, that is to say those compounds of structure $Q(Y_xZ_e)_b$, which have one, two or a plurality of acrylate and/or methacrylate groups preferably two or a plurality of acrylate and/or methacrylate groups.

The polymers and composite materials obtainable with the monomers of component (b1) to be used according to the invention have a pronounced hydrophobia which inter alia manifests itself in very low water absorption of the polymers and composite materials. Additionally, the polymers obtainable by using the monomers of component (b1) to be used according to the invention are characterized by high mechanical stability which inter alia manifests itself in a high flexural strength of the polymers. The monomers of component (b1) to be used according to the invention, in particular according to the particularly preferred configurations and embodiments, lend themselves to processing into polymers which have both a low water absorption and a high flexural strength.

The monomers of component (b1) are copolymerizable with the further monomers of component (b2), wherein the cured polymers or molding materials have low shrinkage, good adherence to various substrates, high resistance to hydrolysis, low water absorption and high mechanical strength. The stated characteristics are in particular important in the area of dental engineering.

The preferred and particularly preferred compounds of component (b1) to be used according to the invention, in particular, allow a high degree of cross-linking and are also preferably radically cross-linkable. Due to their highly functionalized structure they have a high probability of cross-linking and polymerization.

Preferred compounds of component (b1) to be used according to the invention are those wherein Q represents a polyalicyclic structure element, preferably a saturated polyalicyclic structure element, selected from the group consisting of bicylic or tricylic hydrocarbon radicals, wherein preferably none of the hydrogen atoms of this polyalicyclic structure element Q not substituted by substituents $Y_xZ_e$ is substituted.

Particularly preferred are for monomers $Q(Y_xZ_e)_b$ to be used according to the invention whose polyalicylic structure element Q is derived from one of the following tricyclic hydrocarbons: tricyclo[5.2.1.0$^{2,6}$]decane (TCD), tricyclo[5.2.1.0$^{2,6}$]dec-3-ene or tricyclo[3.3.1.1$^{3,7}$]decane (adamantane), i.e. preference is for compounds according to the invention, which have a TCD structure, a tricyclo[5.2.1.0$^{2,6}$]dec-3-ene structure or an adamantane structure.

The stated particularly preferred compounds to be used according to the invention, in which the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical, are preferably those with a tricyclo[5.2.1.02$^{2,6}$]decane structure, a tricyclo[5.2.1.0$^{2,6}$]dec-3-ene structure, a tricyclo[3.3.1.1$^{3,7}$]decane structure or a bicyclo[2.2.1]heptane structure, in which none of the hydrogen atoms of this polyalicyclic structure element Q not substituted by substituents $Y_xZ_e$ is substituted.

Particularly preferred compounds $Q(Y_xZ_e)_b$ of component (b1) to be used according to the invention are those wherein the structure element Q represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical, and particularly preferred the structure element Q represents a tricyclo[5.2.1.0$^{2,6}$]decane radical or a tricyclo[5.2.1.0$^{2,6}$]dec-3-ene radical.

Particularly preferred compounds $Q(Y_xZ_e)_b$ of component (b1) to be used according to the invention are those in which the structure element Q is a tricyclo[5.2.1.0$^{2,6}$]-decane or tricyclo[5.2.1.0$^{2,6}$]-decene structure element and Z preferably is selected from the group consisting of —O—(C=O)—CH=CH$_2$ and —O—(C=O)—C(CH$_3$)=CH$_2$, wherein in turn the group Z is particularly preferably —O—(C=O)—C(CH$_3$)=CH$_2$.

Particularly preferred composite materials according to the invention or to be used or applied according to the invention contain as component (b1) one, two or a plurality of compounds of structure $Q(Y_xZ_e)_b$, which in each case have a tricyclo[5.2.1.0$^{2,6}$]-decane or tricyclo[5.2.1.0$^{2,6}$]-decene structure element and Z preferably is selected from the group consisting of —O—(C=O)—CH=CH$_2$ and —O—(C=O)—C(CH$_3$)=CH$_2$, wherein in turn the group Z is particularly preferably —O—(C=O)—C(CH$_3$)=CH$_2$.

Preference is for the use of methacrylic acid or acrylic acid esters with a tricyclo[5.2.1.0$^{2,6}$]-decane or tricyclo[5.2.1.0$^{2,6}$]-decene structure element, selected from the group consisting of
  8,9-bis(acryloxymethyl)tricyclo[5.2.1.0$^{2,6}$]decane
  8,9-bis(methacryloyloxymethyl)tricyclo[5.2.1.0$^{2,6}$]decane
  8,9-[bis(2-vinyloxyethyl)oxymethyl]tricyclo[5.2.1.0$^{2,6}$]dec-3-ene
  8,9-[bis(2-vinyloxyethyl)oxymethyl]tricyclo[5.2.1.0$^{2,6}$]decane
  8-hydroxymethyl-9-(2-vinyloxyethyl)oxymethyl]tricyclo[5.2.1.0$^{2,6}$]dec-3-ene
  9-hydroxymethyl-8-(2-vinyloxyethyl)oxymethyl]tricyclo[5.2.1.02$^{2,6}$]dec-3-ene
  8,9-bis(acryloyloxymethyl)tricyclo[5.2.1.0$^{2,6}$]dec-3-ene
  8,9-bis(methacryloyloxymethyl)tricyclo[5.2.1.0$^{2,6}$]dec-3-ene
  diacrylic acid esters or dimethacrylic acid esters of compounds selected from the group consisting of:
    3,8-dihydroxymethyl-tricyclo[5.2.1.0$^{2,6}$]decane
    3,9-dihydroxymethyltricyclo-[5.2.1.0$^{2,6}$]decane
    4,8-dihydroxymethyltricyclo[5.2.1.0$^{2,6}$]decane
    3,8-dihydroxytricyclo[5.2.1.0$^{2,6}$]decane
    3,9-dihydroxytricyclo-[5.2.1.0$^{2,6}$]decane
    4,8-dihydroxytricyclo[5.2.1.0$^{2,6}$]decane
  methacrylic acid or acrylic acid esters of compounds from the group consisting of:
    poly(hydroxymethyl)tricyclo[5.2.1.0$^{2,6}$]decanyl-siloxanes
    oxyalkylated bishydroxymethyltricyclo[5.2.1.0$^{2,6}$]decane
    oxyalkylated bishydroxytricyclo[5.2.1.0$^{2,6}$]decane
  urethane- or urea groups-containing methacrylic acid or acrylic acid esters of compounds selected from the group consisting of:
    3,8-dihydroxymethyl-tricyclo[5.2.1.0$^{2,6}$]decane
    4,8-dihydroxymethyl-tricyclo[5.2.1.0$^{2,6}$]decane
    3,9-dihydroxymethyl-tricyclo[5.2.1.0$^{2,6}$]decane
    4,9-dihydroxymethyl-tricyclo[5.2.1.0$^{2,6}$]decane Here in the stated compounds hydrogen in the tricyclo [5.2.1.0$^{2,6}$]-decane- or tricyclo[5.2.1.0$^{2,6}$]-decene radical can be substituted by alkyl groups (here preferably C1-C4-alkyl), alkoxy groups (here preferably C1-C4-alkoxy), halogen atoms (here preferably F) or trifluoromethyl groups.

Many of the radically polymerizable methacrylic acid or acrylic acid esters listed above with a TCD structure element are known from the prior art.

Our own research has shown that with the abovementioned monomers Q(Y$_x$Z$_e$)$_b$ of component (b1) with a tricyclo [5.2.1.0$^{2,6}$]-decane structure element of component (b1) composite materials with low contact angles to the dry tooth enamel (preferably of less than 40°, preferably less than 30°) or lower abrasion (preferably less than 100 μm, preferably less than 80 μm, more preferably less than 70 μm, determined according to the ACTA method) can be obtained.

Our own research has also shown that with the abovementioned monomers Q(Y$_x$Z$_e$)$_b$ of component (b1) with a tricyclo [5.2.1.0$^{2,6}$]-decane structure element—in the cured state—composite materials with lower water absorption (preferably less than 13 μg/mm$^3$, preferably less than 10 μg/mm$^3$) can be obtained.

Y is preferably a structure element that in the structure Q(Y$_x$Z$_e$)$_b$ links the polyalicyclic structure element Q with e structure elements Z and contains or consists of a structure element that is selected from the group consisting of

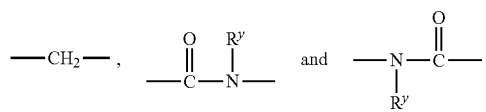

wherein R$^y$ represents another radical of the compound and wherein in each case the bond arranged to the left of the graphic formula is closer to the structure element Q and the bond arranged on the right is closer to the structure element Z.

The other radical R$^y$ of a compound according to the invention or to be used according to the invention of structure Q(Y$_x$Z$_e$)$_b$ is preferably selected from the group consisting of hydrogen, linear, branched or ring-comprising structure elements with 1 through 50 C atoms and 0 through 12 heteroatoms, wherein the heteroatoms that are present optionally are preferably selected from the group consisting of N and O.

The other radical R$^y$ here is preferably selected from the group consisting of hydrogen, linear, branched or ring-comprising structure elements with 1 through 40 C atoms and 0 through 10 heteroatoms, wherein the heteroatoms that are present optionally are preferably selected from the group consisting of N and O.

The other radical R$^y$ here is particularly preferably selected from the group consisting of hydrogen, linear, branched or ring-comprising structure elements with 1 through 35 C atoms and 1 through 10 heteroatoms, wherein the heteroatoms that are present optionally are preferably selected from the group consisting of N and O.

Here Y is preferably a structure element containing or consisting of a structure element selected from the group consisting of

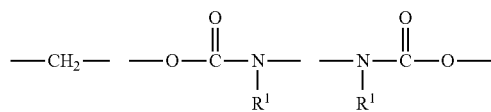

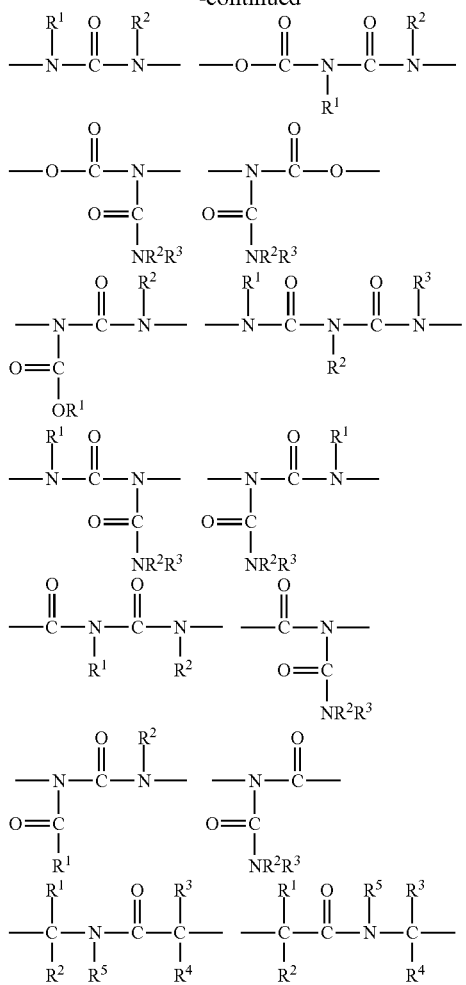

wherein R$^1$, R$^2$, R$^3$R$^4$ and R$^5$ represent other radicals of the compound, wherein in each case the bond arranged to the left of the graphic formula is closer to the structure element Q and the bond arranged on the right is closer to the structure element Z.

The abovementioned radicals R$^1$, R$^2$R$^3$, R$^4$ or R$^5$ of a compound according to the invention or a compound to be used according to the invention of structure Q(Y$_x$Z$_e$)$_b$ are, in each case independently of one another, preferably selected from the group consisting of hydrogen, linear, branched or ring-comprising structure elements with 1 through 30 C atoms and 0 through 10 heteroatoms, wherein the heteroatoms that are present optionally are preferably selected from the group consisting of N and O.

Here the other radicals R$^1$, R$^2$, R$^3$, R$^4$ or R$^5$, in each case independently of one another, are preferably selected from the group consisting of hydrogen, linear, branched or ring-comprising structure elements with 1 through 25 C atoms and 0 through 8 heteroatoms, wherein the heteroatoms that are present optionally are preferably selected from the group consisting of N and O.

Here the other radicals R$^1$, R$^2$, R$^3$, R$^4$ or R$^5$, in each case independently of one another, are particularly preferably selected from the group consisting of hydrogen, linear, branched or ring-comprising structure elements with 1 through 20 C atoms and 0 through 5 heteroatoms, wherein the heteroatoms that are present optionally are selected from the group consisting of N and O.

In compounds of structure $Q(Y_xZ_e)_b$ according to the invention or to be used according to the invention that can be synthesized with comparatively low effort Y is a structure element, containing a structure element or consisting of this, which is selected from the group consisting of

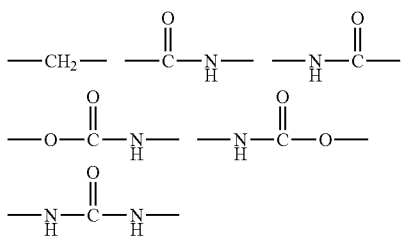

wherein in each case the bond arranged to the left of the graphic formula is closer to the structure element Q and the bond arranged on the right is closer to the structure element Z.

The compounds of structure $Q(Y_xZ_e)_b$ according to the invention or to be used according to the invention can be obtained by the preparation methods known to a person skilled in the art.

Compounds according to the invention or to be used according to the invention of structure $Q(Y_xZ_e)_b$ with an amide structure element can for example be obtained by reacting (i) an educt compound with an isocyanate group and (ii) an educt compound with a carboxylic acid group.

Compounds according to the invention or to be used according to the invention of structure $Q(Y_xZ_e)_b$ with a urethane structure element can for example be obtained by reacting (i) an educt compound with an isocyanate group and (ii) an educt compound with an alcohol group.

Compounds according to the invention or to be used according to the invention of structure $Q(Y_xZ_e)_b$ with a urea structure element can for example be obtained by reacting (i) an educt compound with an isocyanate group and (ii) an educt compound with an amino group.

Compounds according to the invention or to be used according to the invention of structure $Q(Y_xZ_e)_b$ with an allophanate structure element can for example be obtained by reacting (i) an educt compound with a urethane group and (ii) an educt compound with an isocyanate group.

Compounds according to the invention or to be used according to the invention of structure $Q(Y_xZ_e)_b$ with a biuret structure element can for example be obtained by reacting (i) an educt compound with a urea group and (ii) an educt compound with an isocyanate group.

Compounds according to the invention or to be used according to the invention of structure $Q(Y_xZ_e)_b$ with an N-acyl urea structure element can for example be obtained by reacting (i) an educt compound with an amide group and (ii) an educt compound with an isocyanate group.

In a preferred configuration of a composite material to be applied according to the invention component (b1) is selected so that this comprises or consists of bis(methacrylolyoxymethyl)tricyclo[5.2.1.0$^{2,6}$]decane and/or bis(acrylolyoxymethyl)tricyclo[5.2.1.0$^{2,6}$]decane.

In composite materials to be applied according to the invention the methacrylic acid esters, because of their greater biocompatibility are preferred to the corresponding acrylic acid esters, i.e. the Z in compounds of structure $Q(Y_xZ_e)_b$ preferably represents —O—(C═O)—C(CH$_3$)═CH$_2$.

Preferred compounds (monomers) of structure $Q(YZ_e)_b$, of component (b1) are those with one, two, three, four or a plurality of functional groups selected from the group consisting of urethane, urea, N-acyl urea, allophanate, biuret and amide, wherein the amide function is not directly linked with an N atom, an O atom or a carbonyl group.

In the area of dental engineering there is a constant need for further, preferably radically, polymerizable monomers, with which dental materials with certain characteristics are preparable.

Within the context of the present text (meth)acrylic means both acrylic and methacrylic.

EP 1 238 993 describes a method for producing polyisocyanates containing acyl urea groups and blends of these and their use as starting components for the preparation of polyurethane synthetic materials.

EP 0 209 700 A2 and DE 35 22 005 describe (meth)acrylic acid derivatives of certain tricyclodecenes with divalent bridge members from the group of urethanes or ureas, which can be used in the area of dentistry.

EP 0 000 194 A1 (corresponding to U.S. Pat. No. 4,160,080) describes polyisocyanates, containing allophanate groups. These allophanate polyisocyanates may be used for the preparation of polyurethane foams, elastomers, duromers, coatings, adhesives and lacquers.

EP 0 682 012 B1 relates to a method for the preparation of bright-colored, light stable (cyclo-aliphatic) polyisocyanates containing allophanate groups, by reacting organic compounds having urethane groups with organic polyisocyanates with (cyclo)aliphatically bonded isocyanate groups in the presence of tin(II) salts. The polyisocyanates described in EP 0 682 012 B1 can be used as synthesis components in the preparation of polyurethane synthetic materials.

EP 1 727 846 B1 discloses a method for preparation of binding agents containing allophanate groups, comprising groups reacting with ethylenically unsaturated compounds under polymerization under the effects of actinic radiation.

EP 0 712 840 B1 relates to a method for producing certain polyisocyanates comprising allophanate groups through the reaction of compounds containing urethane groups with the formation of allophanate. The compounds according to EP 0 712 840 B1 can be used as binding agents or binding agent components in coating media.

EP 0 867 457 B1 discloses an ethylenically unsaturated polyurethane, which is substantially free from isocyanate groups, which is the reaction product of an ethylenically unsaturated polyisocyanate, containing allophanate groups and β,γ-ethylenically unsaturated ether groups, with a hydroxyfunctional, ethylenically unsaturated compound, wherein the ethylenically unsaturated polyisocyanate is prepared by allophantization of the urethane groups-containing reaction products of an organic diisocyanate with a β,γ-ethylenically unsaturated ether alcohol, which is selected from the group consisting of glycerin diallyl ether, trimethylolpropane diallyl ether and pentaerythritriallyl ether. The ethylenically unsaturated polyurethanes with allophanate groups disclosed in EP 0 867 457 B1 can be used as binding agents in single component coating compositions.

DE 10 2007 040 240 A1 and EP 1 645 582 A1 in each case describe a method for preparation of radiation-curing allophanates through the reaction of compounds containing isocyanate groups and hydroxyfunctional compounds, wherein the ratio of NCO groups to OH groups is 1.45:1.0 through 1.1:1.0. According to DE 10 2007 040 239 A1 with the use of certain mixtures containing hydroxyethylacrylate and hydroxypropylacrylate as the hydroxyfunctional compounds corresponding radiation-curing allophanates are obtained. The radiation-curing allophanates according to these three documents can be used for the preparation of coatings and lacquers, as well as adhesives, inks, casting resins, dental compounds, release agents, photoresists, stereolithography systems, resins for composites and sealants.

DE 10 2004 060 285 A1 relates to radiation-curable compounds based on a dicidol mixture (containing two or three isomers 3,8-, 4,8- and/or 5,8-bis(hydroxymethyl)tricyclo [5.2.1.0$^{2,6}$]decane) with at least one compound, having at least one ethylenically unsaturated grouping with simultaneously at least one reactive grouping in relation to dicidol, wherein this compound may be a reaction product of hydroxyalkyl(meth)acrylate and diisocyanate. The compositions according to DE 10 2004 060 285 A1 can be used as radiation-induced-curing coating materials, adhesives, laminations, printing and other inks, polishes, varnishes, pigment pastes, fillers, cosmetic materials, packaging materials and/or sealing and/or insulating materials.

WO 2006/063891 A1 discloses radically polymerizable compounds, substantially containing the reaction product of a dicidol mixture and at least one compound, which has at least one ethylenically unsaturated grouping with simultaneously at least one reactive grouping in relation to dicidol. The areas of application correspond to those mentioned in DE 10 2004 060 285 A1.

U.S. Pat. No. 6,670,499 B1 describes diurethanes derived from adamantane. The compounds described in U.S. Pat. No. 6,670,499 are suitable as intermediate products for use in dentistry or for producing optical materials (such as lenses, for example).

Thus a further object for the present invention was to provide novel, preferably radically polymerizable monomers, which in a composite material according to the invention or to be used according to the invention or to be applied according to the invention, in particular in a dental composite material according to the invention, can be used in or as a constituent of component (b1).

Preferably, the polymers obtainable through the use of the monomers should have a pronounced hydrophobia which inter alia manifests itself in very low water absorption. Similarly preferably, the polymers obtainable through the use of monomers should be characterized by high mechanical stability which inter alia manifests itself in a high flexural strength. Particularly preferably, through the use of monomers it should be possible to prepare polymers that have both a low water absorption and a high flexural strength as well as an exceptional surface affinity.

This further object is achieved by a compound of structure $Q(YZ_e)_b$ (wherein each Y is selected independently of any other structure elements Y) with one, two, three, four or a plurality of functional groups selected from the group consisting of N-acyl urea, allophanate, biuret and amide, wherein the amide function is not directly linked with an N atom, an O atom or a carbonyl group, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $YZ_e$ are substituted by alkyl groups (here preferably C1-C4-alkyl), alkoxy groups (here preferably C1-C4-alkoxy), halogen atoms (here preferably F) or trifluormethyl groups, b is an integer selected from the group of integers 2, 3, 4, each Z represents a structure element, which independently of any other structure elements Z is selected from the group consisting of

—O—(C=O)—CH=CH$_2$, —O—(C=O)—C(CH$_3$)=CH$_2$,

—(C=O)—CH=CH$_2$, —(C=O)—C(CH$_3$)=CH$_2$,

—CH=CH$_2$, —C(CH$_3$)=CH$_2$ and —O—CH=CH$_2$, each index e is an integer, which independently of any other indices e is selected from the group of integers 1, 2, 3 and 4, each Y represents a structure element, which in the structure $Q(YZ_e)_b$ binds the polyalicyclic structure element Q with e structure elements Z, wherein the compound is a first reaction product of a first reaction of A) a compound of structure $QG_b$, in which each G represents a reactive group, which independently of other groups G is selected from the group consisting of (—CH$_2$)$_n$—NH$_2$, (—CH$_2$)$_n$(OCH$_2$—CHR)$_m$—OH, (—CH$_2$)$_n$—NCO and (—CH$_2$)—COOH with B) two or a plurality of identical or different compounds $MZ_e$, wherein M represents a structure element which in each case has one or a plurality of grouping(s) that react with the groups G selected from the group consisting of —NH, —NH$_2$, —OH, —NCO and —COOH, wherein the following applies:

R, in each case independently of any other R, represents a hydrogen atom or an alkyl radical; preferably R represents a hydrogen atom or a linear or branched alkyl radical with 1 through 6 C atoms; more preferably R represents a hydrogen atom or a methyl radical, m is an integer selected from the group of integers from 0-10, each index n is an integer, which independently of any other indices n is selected from the group consisting of 0 and 1, or the compound is a second reaction product from a reaction of the above first reaction product with C) a further compound according to A) or B), wherein each further compound according to A) or B) has the above meaning, independently of what A) and/or B) represent in the first reaction, or the compound is a third reaction product from a reaction of the above second reaction product with D) a further compound according to A) or B), wherein each further compound according to A) or B) has the above meaning, independently of what A) and/or B) represent in the first and/or second reaction.

From that stated above it can be inferred that in compounds to be used according to the invention containing an amide group (as defined) this amide group is not a component of the urethane group.

Also preferred are compounds to be used according to the invention of structure $Q(YZ_e)_b$ (wherein each Y is selected independently of any other structure elements Y) of component (b1) with one, two, three, four or a plurality of functional groups selected from the group consisting of N-acyl urea, allophanate, biuret and amide, wherein the amide function is not directly linked with an N atom, an O atom or a carbonyl group, wherein the amide in turn preferably represents (meth) acrylamide.

In preferred compounds to be used according to the invention of structure $Q(YZ_e)_b$ (wherein each Y is selected independently of any other structure elements Y), the linking between Q and at least one structure element Z takes place via a bridge which contains or comprises a divalent bridge member, selected from the group consisting of

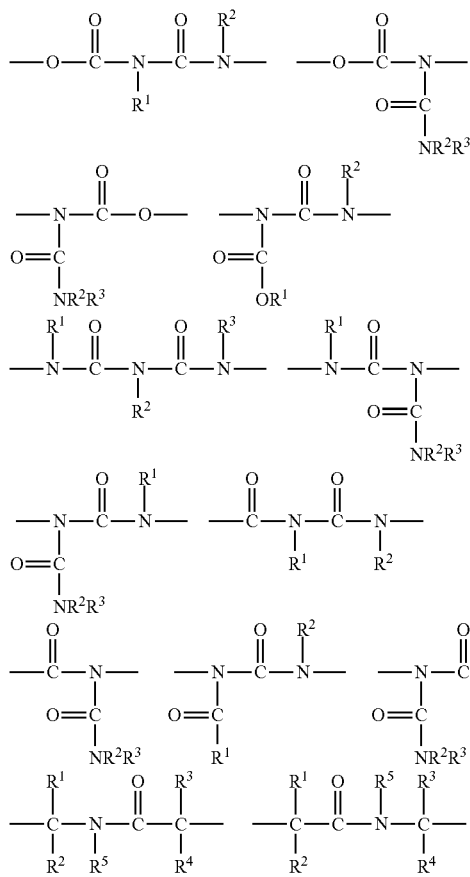

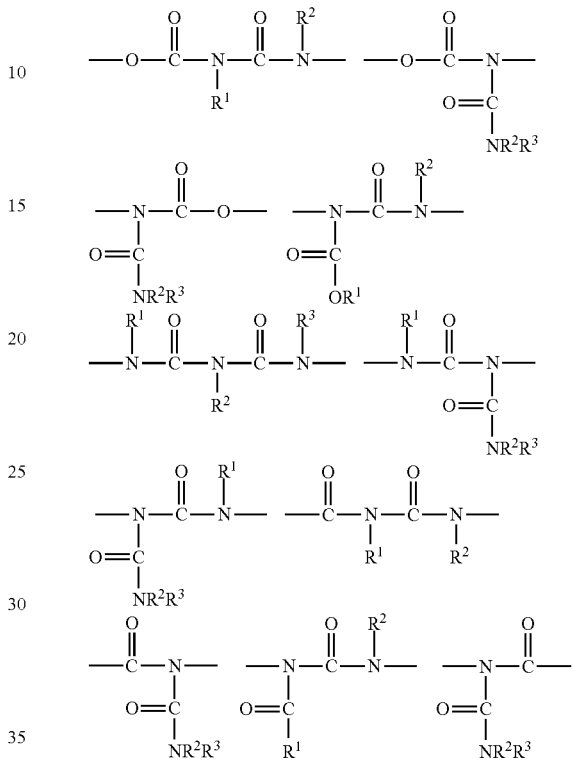

wherein $R^1$, $R^2$, $R^3 R^4$, $R^5$ represent other radicals of the compound, wherein in each case the bond arranged to the left of the graphic formula is closer to the structure element Q and the bond arranged on the right is closer to the structure element Z.

The further object is likewise solved by novel compounds of structure $Q(Y_x Z_e)_b$ with x=1 with one, two, three, four or a plurality of functional groups that are selected from the group consisting of N-acyl urea, allophanate and biuret, wherein the following applies:

Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element Q not substituted by substituents $YZ_e$ is or are substituted by alkyl groups, alkoxy groups, halogen atoms or trifluormethyl groups;

b is an integer selected from the group of integers 2, 3, 4;

each Z represents a structure element, which independently of any other structure elements Z is selected from the group consisting of

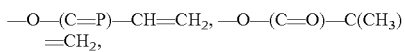

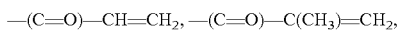

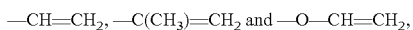

each index e is an integer, which independently of any other indices e is selected from the group of integers 1, 2, 3 and 4;

each Y represents a structure element that in the structure $Q(Y_x Z_e)_b$ with x=1 links the polyalicyclic structure element Q with e structure elements Z and contains or consists of a structure element selected from the group consisting of wherein $R^1$, $R^2$, and $R^3$ represent other radicals of the compound, wherein in each case the bond arranged to the left of the graphic formula is closer to the structure element Q and the bond arranged on the right is closer to the structure element Z. These compounds are eminently suitable as monomers for use in composite materials according to the invention.

Preferably such a compound of structure $Q(Y_x Z_e)_b$ with x=1 comprises two, three, four or a plurality of functional groups selected from the group consisting of N-acyl urea, allophanate and biuret.

In a preferred configuration each index e represents an integer, which independently of any other indices e is selected from the group of integers 2, 3 and 4.

The abovementioned radicals $R^1$, $R^2$ or $R^3$ of a novel compound to be used according to the invention are, in each case independently of one another, preferably selected from the group consisting of hydrogen, linear, branched or ring-comprising structure elements with 1 through 30 C atoms and 0 through 10 heteroatoms, wherein the heteroatoms that are present optionally are preferably selected from the group consisting of N and O.

The other radicals $R^1$, $R^2$ or $R^3$ of a novel compound to be used according to the invention are, in each case independently of one another, preferably selected from the group consisting of hydrogen, linear, branched or ring-comprising structure elements with 1 through 25 C atoms and 0 through 8 heteroatoms, wherein the heteroatoms that are present optionally are preferably selected from the group consisting of N and O.

The other radicals $R^1$, $R^2$ or $R^3$ of a novel compound to be used according to the invention are, in each case independently of one another, preferably selected from the group consisting of hydrogen, linear, branched or ring-comprising structure elements with 1 through 20 C atoms and 0 through 5 heteroatoms, wherein the heteroatoms that are present optionally are selected from the group consisting of N and O.

A novel compound $Q(Y_xZ_e)_b$ with x=1, preferably a compound $Q(Y_xZ_e)_b$ with x=1 as identified above as preferred, to be used in a composite material according to the invention or to be applied according to the invention, is preferably preparable by reacting a first reaction product, which is the reaction product of a first reaction of A) a compound of structure $QG_b$, in which each G represents a reactive group, which independently of other groups G is selected from the group consisting of $(-CH_2)_n-NH_2$, $(-CH_2)_n-(OCH_2-CHR)-$, $-OH$, $(-CH_2)_n-NCO$ and $(-CH_2)_n-COOH$
with B) two or a plurality of identical or different compounds $MZ_e$, wherein M represents a structure element which in each case has one or a plurality of grouping(s) that react with the groups G selected from the group consisting of $-NH$, $-NH_2$, $-OH$, $-NCO$ and $-COOH$, wherein the following applies:
R in each case independently of any other R represents a hydrogen atom or an alkyl radical;
m is an integer selected from the group of integers from 0 through 10,
each index n is an integer, which independently of any other indices n is selected from the group consisting of 0 and 1, wherein the compound is a second reaction product from a reaction of the above first reaction product with C) a further compound according to A) or B), wherein each further compound according to A) or B) has the above meaning, independently of what A) and/or B) represent in the first reaction,
or
the compound is a third reaction product from a reaction of the above second reaction product with D) a further compound according to A) or B), wherein each further compound according to A) or B) has the above meaning, independently of what A) and/or B) represent in the second reaction.

A compound preferably to be used according to a preferred configuration is a second reaction product from a reaction of the above first reaction product with C) a further compound according to A) or B), wherein each further compound according to A) or B) has the same meaning as in the first reaction,
and/or
wherein the compound is a third reaction product from a reaction of the above second reaction product with D) a further compound according to A) or B), wherein each further compound according to A) or B) has the same meaning as in the first and/or the second reaction, preferably as in the first and the second reaction.

In a first embodiment m=0. This applies to all aspects of the present invention.

In preferred compounds to be used according to the invention the link between Q and at least one structure element Z takes place via a bridge which contains or comprises a divalent bridge member, selected from the group consisting of

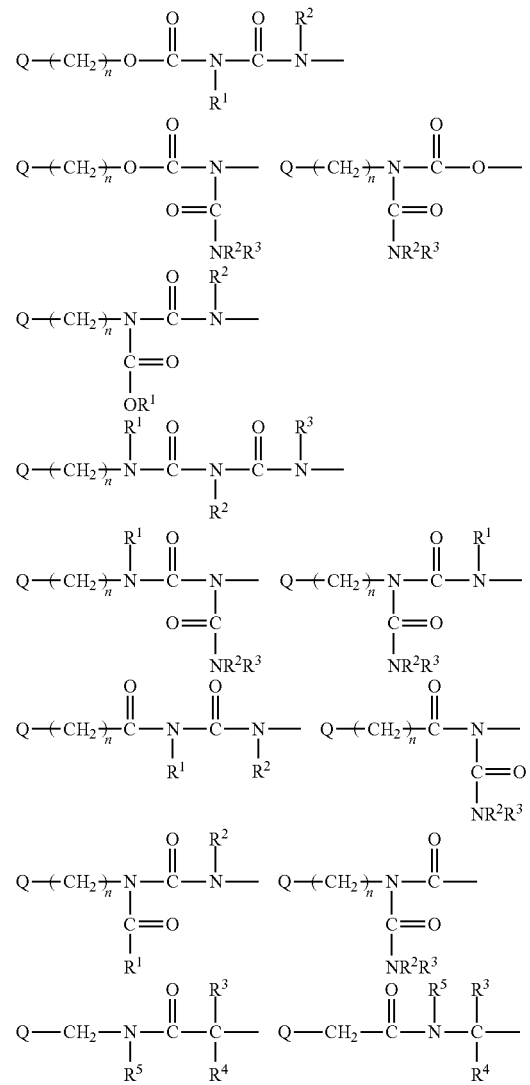

wherein $R^1$, $R^2$, $R^3$, $R^4$, $R^5$ represent other radicals of the compound and Q and the index n have the meaning indicated above.

The bond shown on the right of each graphic formula is closest to the structure element Z.

In a preferred configuration a novel compound to be used according to the invention $Q(Y_xZ_e)_b$ with x=1, preferably a compound $Q(Y_xZ_e)_b$ with x=1 as identified above or below as preferred, comprises one or a plurality of structure elements selected from the group consisting of

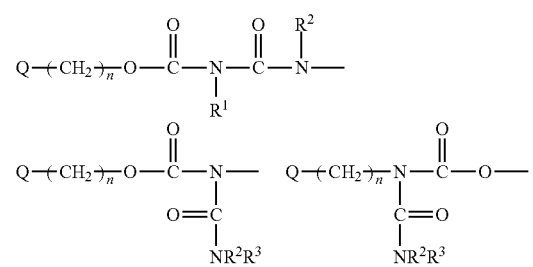

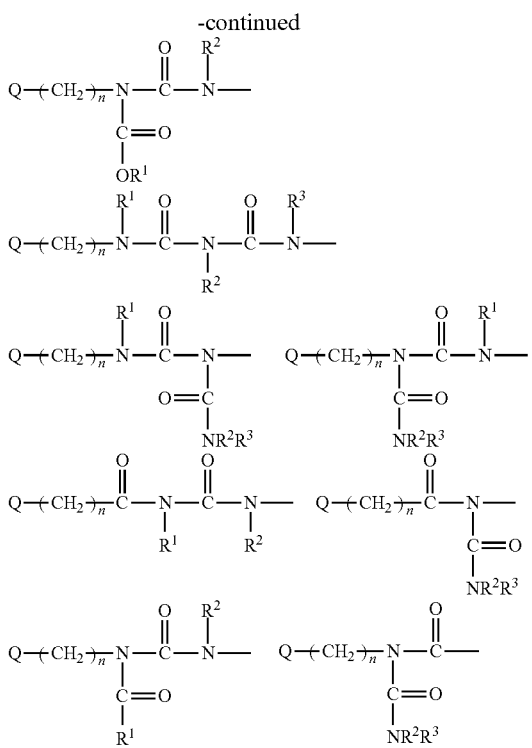

wherein $R^1$, $R^2$ and $R^3$ represent other radicals of the compound (and preferably have the abovementioned preferred meaning) and Q has the abovementioned meaning and the index n is selected from the group consisting of 0 and 1.

As already mentioned above preferred novel compounds to be used according to the invention are those wherein Q represents a saturated polyalicyclic structure element, selected from the group consisting of bicylic and tricylic hydrocarbon radicals, wherein preferably none of the hydrogen atoms of this polyalicyclic structure element Q not substituted by substituents $YZ_e$ is substituted.

Particularly preferred novel compounds to be used according to the invention are those wherein the structure element Q represents a tricyclo[5.2.1.0$^{2,6}$]decane radical, a tricyclo [5.2.1.0$^{2,6}$]dec-3-ene radical, a tricyclo[3.3.1.1$^{3,7}$]decane radical or a bicyclo[2.2.1]heptane radical.

Preferred novel compounds to be used according to the invention of component (b1) are those wherein Q represents a tricyclic hydrocarbon radical, wherein preferably none of the hydrogen atoms of this tricyclic hydrocarbon radical not substituted by substituents $YZ_e$ (wherein each Y is selected independently of any further structure elements or is omitted) is substituted.

Particularly preferred novel compounds to be used according to the invention are those wherein the structure element Q represents a tricyclo[5.2.1.0$^{2,6}$]decane radical, a tricyclo [5.2.1.0$^{2,6}$]dec-3-ene radical or a tricyclo[3.3.1.1$^{3,7}$]decane radical, more preferably a tricyclo[5.2.1.0$^{2,6}$]decane radical or a tricyclo[3.3.1.1$^{3,7}$]decane radical.

Preference is for novel compounds to be used according to the invention in which (i) the structure element Z represents —O—(C=O)—C(CH$_3$)=CH$_2$, wherein the functional groups are allophanate, biuret or acyl urea groups, since with these compounds particularly good results have been obtained, and/or (ii) the structure element Q represents a tricyclo[5.2.1.0$^{2,6}$] decane radical.

Greater preference is for novel compounds to be used according to the invention, in which the structure element Z represents —O—(C=O)—C(CH$_3$)=CH$_2$, wherein the functional groups are allophanate, biuret or acyl urea groups and the structure element Q represents a tricyclo[5.2.1.0$^{2,6}$] decane radical.

Preference is for novel compounds to be used according to the invention in which all photocurable groups present correspond to the structure element Z.

Preference is for novel compounds to be used according to the invention in which all terminal polymerizable groups present correspond to the structure element Z.

A novel compound to be used according to the invention, apart from photocurable groups of the structure element Z, can also comprise other polymerizable, preferably terminal polymerizable groups, which are not photocurable, in particular not under the normal photocuring conditions that exist in dentistry. This is generally not preferred, however, since such groups do not contribute towards the desired characteristics of the product that exists following polymerization.

Further preferred compounds to be used according to the invention are those in which at least one structure element $YZ_e$ is selected independently of the other structure elements $YZ_e$, and preferably all structure elements $YZ_e$ are selected from the group consisting of

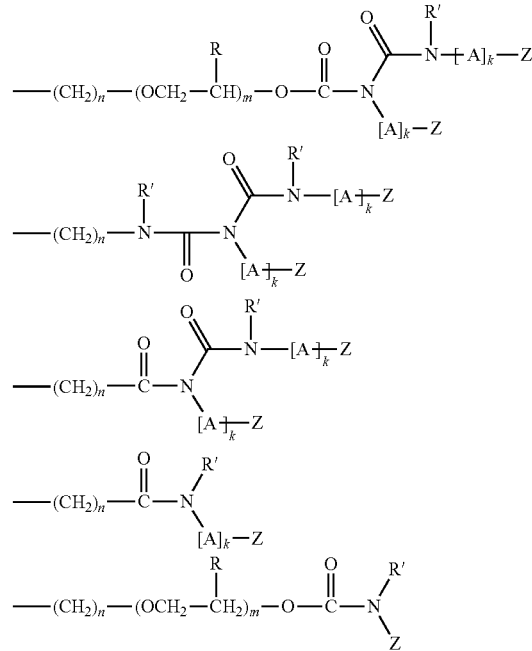

wherein Z, R, m and n have the meaning given above and wherein the following also applies:
  each A represents a divalent organic bridge member,
  each index k is an integer, which independently of any other indices k is selected from the group consisting of 0 and 1;
  each R' represents a structure element which independently of any other structure elements R' is selected from the group consisting of H and a structure element (C=O)—NH-(A)$_k$-Z, wherein A, Z and k in turn have the meanings given above.

In a preferred embodiment m=0.

Similarly preferred compounds to be used according to the invention are those in which at least one structure element $YZ_e$ is selected independently of the other structure elements $YZ_e$, and preferably all structure elements $YZ_e$ are selected from the group consisting of

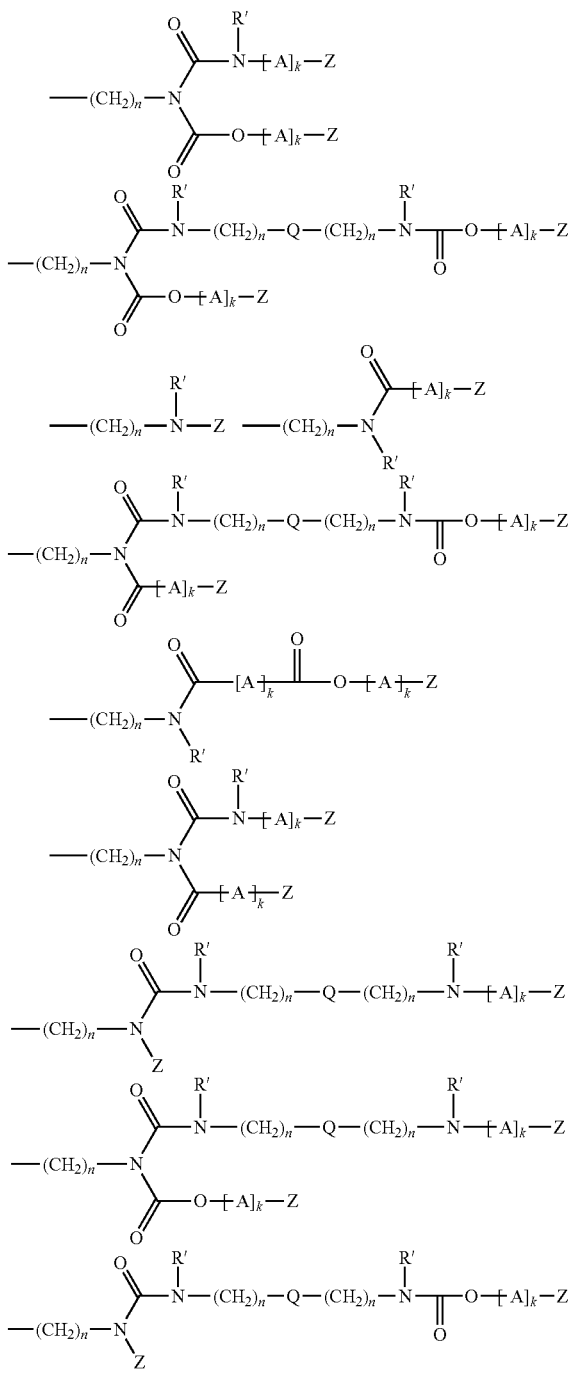

wherein each Q independently of any other structure elements Q has the above meaning and wherein Z, A, k and R', as well as n, have the above meaning.

In a preferred configuration the present invention relates to a compound to be used according to the invention $Q(Y_xZ_e)_b$ with x=1, preferably a compound to be used according to the invention $Q(Y_xZ_e)_b$ with x=1 as identified above or below as preferred, wherein
at least one structure element $YZ_e$ is selected independently of the other structure element(s) $YZ_e$, and preferably all structure elements $YZ_e$ are selected
from the group consisting of

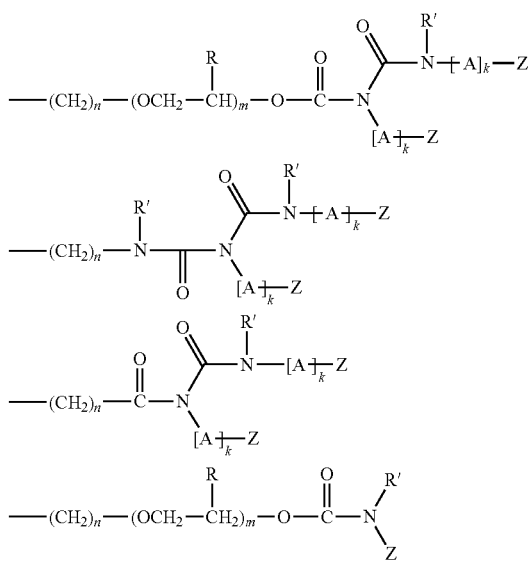

wherein Z, R, m and n have the meaning given above and wherein the following also applies:
each A represents an organic structure element,
each index k is an integer, which independently of any other indices k is selected from the group consisting of 0 and 1;
each R' represents a structure element which independently of any other structure elements R' is selected from the group consisting of H and a structure element (C=O)—NH-(A)$_k$-Z, wherein A, Z and k in turn have the meanings given above.

In a preferred configuration the present invention relates to a novel compound to be used according to the invention $Q(Y_xZ_e)_b$ with x=1, preferably a compound to be used according to the invention $Q(Y_xZ_e)_b$ with x=1 as identified above or below as preferred, wherein
at least one structure element $YZ_e$ is selected independently of the other structure element(s) $YZ_e$, and preferably all structure elements $YZ_e$ are selected
from the group consisting of

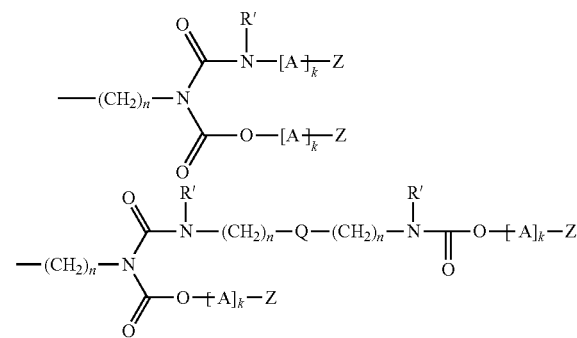

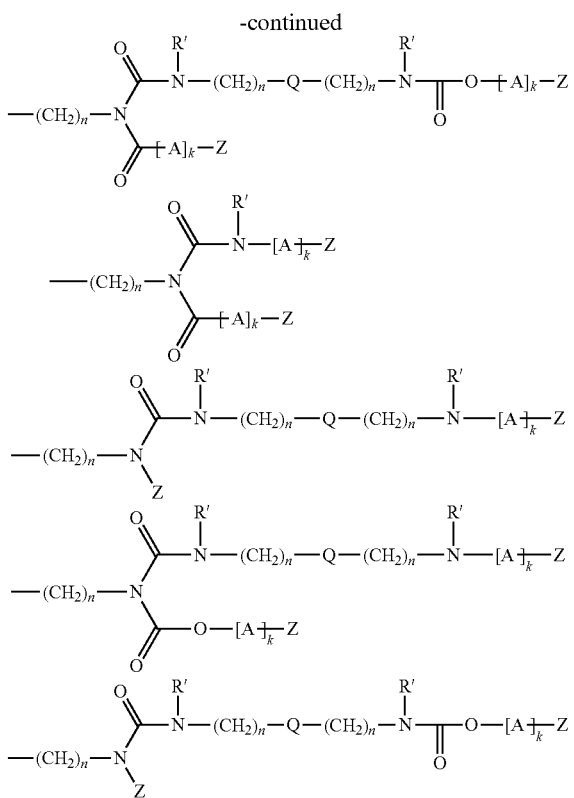

wherein each Q independently of any other structure elements Q has the above meaning, and
wherein Z and n have the abovementioned meaning and wherein the following also applies:

each A represents an organic structure element,
each index k is an integer, which independently of any other indices k is selected from the group consisting of 0 and 1;
each R' represents a structure element which independently of any other structure elements R' is selected from the group consisting of H and a structure element (C=O)—NH-(A)$_k$-Z, wherein A, Z and k in turn have the meanings given above.

Here in turn preference is for compounds to be used according to the invention in which each structure element A independently of any other structure elements A is selected from the group consisting of all linear, branched or ring-comprising divalent organic bridge members with 1 through 25 C atoms and optionally 1 through 10, preferably 1 through 5 heteroatoms, wherein the heteroatoms that are optionally present are preferably selected from the group consisting of N and O.

Here in turn preference is for a compound to be used according to the invention in which each structure element A independently of any other structure elements A is selected from the group consisting of linear, branched or ring-comprising structure elements with 1 through 25 C atoms and 0 through 10 heteroatoms, preferably with 1 through 5 heteroatoms, wherein the heteroatoms that are optionally present are preferably selected from the group consisting of N and O.

Further preference is for compounds in which each structure element A independently of any other structure elements A is selected from the group consisting of ($C_1$-$C_{20}$) alkylene, ($C_1$-$C_{20}$) heteroalkylene, ($C_3$-$C_{20}$) cycloalkylene, ($C_4$-$C_{20}$) cycloalkylalkylene, ($C_2$-$C_{20}$) alkenylene, ($C_3$-$C_{20}$) cycloalkenylene, C($C_4$-$C_{20}$) cycloalkenylalkylene, ($C_4$-$C_{20}$) cycloalkenylenalkylene, ($C_3$-$C_{25}$) arylene, ($C_2$-$C_{25}$) heteroarylene, ($C_4$-$C_{25}$) arylalkylene, $C_4$-$C_{25}$) arylenalkylene, ($C_4$-$C_{25}$) arylheteroalkylene, and ($C_4$-$C_{25}$) arylenheteroalkylene.

In preferred configurations structure element A comprises one or a plurality of the following atoms or groups of atoms:

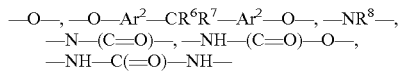

wherein the following applies:

$Ar^1$ and $Ar^2$ independently of each other represent an aromatic ring which is optionally substituted, here preferably once or a plurality of times substituted with $C_1$-$C_4$ alkyl radicals, here in turn preferably a phenyl ring.

$R^6$, $R^7$ and $R^8$ independently of one another represent hydrogen or a $C_1$-$C_8$ radical, here preferably a $C_1$-$C_4$ alkyl radical, here in turn preferably methyl or ethyl.

For the preparation of the stated compounds of structure $Q(YZ_e)_b$ or $Q(Y_xZ_e)_b$ preferably hydroxyl compounds of (meth)acrylates can be used, wherein mixtures of acrylates and methacrylates can also be used. Preference for use as reaction partners according to components B), C) or D) is for: alkylene oxide mono(meth)acrylates such as for example ethylene glycol mono(meth)acrylate, diethylene glycol mono(meth)acrylate, triethylene glycol mono(meth)acrylate, tetraethylene glycol mono(meth)acrylate, etc., polyalkylene oxide mono(meth)acrylates such as for example polyethylene glycol mono(meth)acrylate, polypropylene glycol mono (meth)acrylate, polybutylene glycol mono(meth)acrylate, etc., hydroxyalkyl mono(meth)acrylates such as for example hydroxyethyl(meth)acrylate, hydroxypropyl(meth)acrylate, 2-hydroxypropyl(meth)acrylate, hydroxybutyl(meth)acrylate, 4-hydroxybutyl(meth)acrylate, hydroxypentyl(meth) acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate, hydroxydodecyl(meth)acrylate, etc., poly(ε-caprolactone)mono(meth)acrylate, poly(γ-caprolactone)mono(meth) acrylate, etc., the mono-, di-, tetra-, or penta(meth)acrylates of polyhydric alcohols, such as glycerin, such as for example glycerin di(meth)acrylate (2-hydroxypropyl-1,3-di(meth)acrylate, 3-hydroxypropyl-1,2-di(meth)acrylate), such as trimethylolpropane, such as for example trimethylolpropane di(meth)acrylate, such as pentaerythritol, such as for example pentaerythritoltri(meth)acrylate, such as dipentaerythritol, such as for example dipentaerythritolpenta(meth)acrylate, such as ditrimethylolpropantri(meth)acrylate, such as neopentyl glycol(meth)acrylate, the (meth)acrylates of alkoxylated or phenoxylated glycerin, here preferably the (meth) acrylates of ethoxylated, propoxylated, etc. glycerin, trimethylolpropane, pentaerythritol, dipentaerythritol, ditrimethylolpropane, etc. and the technical mixtures thereof, bisphenol-A-glycidyl-(meth)acrylate (Bis-GMA), bisphenol-B-glycidyl-(meth)acrylate, bisphenol-C-glycidyl-(meth) acrylate, bisphenol-F-glycidyl-(meth)acrylate, alkoxylated bisphenol-A-glycidyl-(meth)acrylate (e.g. ethoxylated bisphenol-A-glycidyl-(meth)acrylate), etc.

For the preparation of the compounds to be used according to the invention as component B) isocyanates can also be used. Preference here is for mono- and diisocyanates.

Preferred diisocyanates are selected from the group consisting of cyclohexane diisocyanate, methylcyclohexane diisocyanate, ethylcyclohexane diisocyanate, propylcyclohexane diisocyanate, methyldiethylcyclohexane diisocyanate, phenylene diisocyanate, toluoylene diisocyanate, bis(isocyanatophenyl)methane, propane diisocyanate, butane diisocyanate, pentane diisocyanate, hexane diisocyanate, such as hexamethylene diisocyanate or 1,5-diisocyanato-2-methyl pentane, heptane diisocyanate, octane diisocyanate, nonane diisocyanate, such as 1,6-diisocyanato-2,4,4-trimethylhexane or 1,6-diisocyanato-2,2,4-trimethylhexane, nonane triisocyanate, such as 4-isocyanatomethyl-1,8-octane diisocyanate, decane di- and triisocyanate, undecane di- and -triisocyanate, dodecandi- and -triisocyanates, isophorone diisocyanate, dicyclohexylmethane-4,4'-diisocyanate, isocyanatomethylmethylcyclohexyl isocyanate, 1,3-bis(isocyanatomethyl)cyclohexane or 1,4-bis(isocyanatomethyl)cyclohexane.

Preferred monoisocyanates are (meth)acryloyl isocyanate and (meth)acryl-$C_2$-$C_8$-alkyl isocyanates (e.g. (meth)acrylalkyl isocyanates with alkyl spacers, having 2 through 8, particularly preferably 2 through 6 carbon atoms), here in turn preference is for (meth)acryl ethyl isocyanate (2-isocyanatoethyl(meth)acrylate).

Furthermore, as component B) monoisocyanates have proven to be an advantage that are the reaction products of amino- or hydroxyalkyl(meth)acrylates, the alkyl spacers of which have 1 through 12, preferably 2 through 8, particularly preferrably 2 through 6 carbon atoms, and diisocyanates.

Preferably to this end a diisocyanate mentioned above is reacted in equimolar proportions with an amino- or hydroxylalkyl compound (indicated above as preferred) of a (meth)acrylate, wherein the hydroxylalkyl compounds in turn are preferably selected from the group consisting of hydroxyethyl(meth)acrylate, hydroxypropyl(meth)acrylate, hydroxybutyl(meth)acrylate, hydroxypentyl(meth)acrylate and hydroxyhexyl(meth)acrylate.

Quoted examples are the reaction products in the molar ratio of 1:1 of hydroxyethylmethacrylate and isophorone diisocyanate, dicyclohexylmethane-4,4'-diisocyanate or hexamethylene diisocyanate.

The present invention further relates to the application or the use of a compound mentioned above, preferably in one of the configurations characterized as preferred or particularly preferred, in a composite material according to the invention or to be applied according to the invention for the stated purposes, preferably in a dental composite material.

The present invention also relates to the use of a compound of structure $Q(YZ_e)_b$ or $Q(Y_xZ_e)_b$ mentioned above preferably in one of the configurations identified as preferred or particularly preferred, for the preparation of a composite material, in particular a dental composite material, particularly a dental sealing material for sealing of fissures, for sealing of pits and for sealing of carious lesions.

The present invention also relates to the stated compounds of structure $Q(YZ_e)_b$ or $Q(Y_xZ_e)_b$, preferably in one of the configurations identified as preferred or particularly preferred, as or for use or application as a dental sealing material, preferably as a sealing material for sealing of fissures, for sealing of pits and for sealing of carious lesions.

The present invention further relates to a method for preparing a compound $Q(YZ_e)_b$ or a mixture comprising at least one compound $Q(YZ_e)_b$ to be used according to the invention, which can be advantageously used in or as component (b1) of a composite material according to the invention or to be applied according to the invention, with the following steps:

In a first reaction, reacting

A) a compound of structure $QG_b$, in which each G represents a reactive group, which is selected independently of other G groups from the group consisting of ($-CH_2$)$_n$$-NH_2$, ($-CH_2$)$_n$$-$(OCH$_2$$-$CHR)$_m$$-$OH, ($-CH_2$)$_n$$-$NCO and ($-CH_2$)$_n$$-$COOH, preferably a compound of structure $QG_b$, in which each G represents a reactive group, which is selected independently of other G groups from the group consisting of $-NH_2$, $-CH_2NH_2$, $-OH$, $-CH_2OH$, $-NCO$, $-CH_2NCO$, and $-COOH$, with B) two or a plurality of identical or different compounds $MZ_e$, wherein M represents a structure element which in each case has one or a plurality of grouping(s) that react with the groups G selected from the group consisting of $-NH$, $-NH_2$, $-OH$, $-NCO$ and $-COOH$ to form a first reaction product, optionally in a second reaction, reacting the first reaction product with C) a further compound according to A) or B), wherein each further compound according to A) or B) has the above meaning, independently of what A) and/or B) represent in the first reaction, to form a second reaction product, and optionally in a third reaction, reacting the second reaction product with D) a further compound according to A) or B), wherein each further compound according to A) or B) has the above meaning, independently of what A) and/or B) represent in the first and/or second reaction.

wherein Q, b, Y, Z, and e in each case have the above meanings, and wherein the following applies:

R, in each case independently of any other R, represents a hydrogen atom or an alkyl radical; preferably R represents a hydrogen atom or a linear or branched alkyl radical with 1 through 6 C atoms; more preferably R represents a hydrogen atom or a methyl radical;

m is an integer selected from the group of integers from 0 through 10, each index n is an integer, which independently of any other indices n is selected from the group consisting of 0 and 1, wherein the ratio of the total number of NCO groups to the total number of $-NH_2$, $-OH$ and $-COOH$ in the total number of compounds according to A) and B) in the first, optionally second and optionally third reaction is greater than or equal to 1, preferably in the range 1.1:1 through 5:1, more preferably in the range 1.25:1 through 4:1, particularly preferably in the range 1.5:1 through 3:1, and most preferably in the range 2:1 through 2.5:1.

Here the ratio of the total number of NCO groups reacted to the total number of $-NH_2$, $-OH$ and $-COOH$ reacted in the total number of compounds according to A) and B) in the first, optionally second and optionally third reaction is preferably in the range 1.1:1 through 5:1, more preferably in the range 1.25:1 through 4:1, particularly preferably in the range 1.5:1 through 3:1, and most preferably in the range 2:1 through 2.5:1.

Preferably the reaction to the first reaction product, to the second reaction product and/or to the third reaction product takes place in the presence of a catalyst.

Preferred catalysts here are tertiary amines or Lewis acids, here in turn preference is for metal salts of higher fatty acids, in particular dibutyltin dilaurate or tin (II) octoate The quantity of catalyst here is preferably in the range 0.01 through 2 wt. %, preferably 0.08 through 1 wt. %, in relation to the total quantity of reactants according to A) and B) and optionally C) and optionally D).

The reaction to the first reaction product, to the second reaction product and/or the third reaction product preferably takes place in a temperature range of 0 through 160° C., preferably in the range 30 through 140° C. and particularly preferably in the range 60 through 120° C. The reaction is preferably carried out at normal pressure (1013 mbar).

The statements above or below relating to the compounds to be used according to the invention identified as preferred and particularly preferred apply to the preferred and particularly preferred configurations of the method, mixtures, blends, products and applications according to the invention accordingly in each case.

In a further aspect the present invention relates to a mixture comprising one, two or a plurality of different compounds to be used according to the invention that is preparable using a method according to the invention.

In the following the invention is initially explained in detail for monomers comprising tricyclic structure elements Q using the example of tricyclo[5.2.1.0$^{2,6}$]decane (TCD)-derivatives.

1.) Starting with the bis(hydroxymethyl)tricyclo[5.2.1.0$^{2,6}$] decane (TCD-diol)

bis(hydroxymethyl)tricyclo[5.2.1.0$^{2,6}$]decane is commercially available, for example as a dicidol mixture of the isomeric compounds 3,8-bis(hydroxymethyl)tricyclo[5.2.1.0$^{2,6}$]decane and 4,8-bis(hydroxymethyl)tricyclo[5.2.1.0$^{2,6}$]decane as well as 3,9-bis(hydroxymethyl)tricyclo[5.2.1.0$^{2,6}$]decane and 4,9-bis(hydroxymethyl)tricyclo[5.2.1.0$^{2,6}$]decane.

The bis(hydroxymethyl)tricyclo[5.2.1.0$^{2,6}$]decanes can, starting with dicyclopentadiene (tricyclo[5.2.1.0$^{2,6}$]deca-3,8-diene), be synthesized. Dicyclopentadiene is easily accessible in a Diels-Alder reaction by dimerization of cyclopentadiene. Hydroformylation of dicyclopentadiene then produces the bis(hydroxymethyl)tricyclo[5.2.1.0$^{2,6}$]decane. According to the synthesis pathway taken bis(hydroxymethyl)tricyclo[5.2.1.0$^{2,6}$]decanes specifically substituted at different positions can be obtained. Thus in published documents JP 7-206740, EP 1 112 995 B1 or EP 0 049 631 B1 specifications are provided on how, for example, the 8,9-bis (hydroxymethyl)tricyclo[5.2.1.0$^{2,6}$]decane is preparable. DE 103 52 260 B3 on the other hand describes a method for preparing 3(4), 8(9)-bis(hydroxymethyl)tricyclo[5.2.1.0$^{2,6}$] decane. The notation of the positions of the hydroxymethyl groups 3(4), 8(9) means 3 or 4, 8 or 9.

The commercially available starting compound that can be used for the preparation of monomers to be used according to the invention, bis(hydroxymethyl)tricyclo[5.2.1.0$^{2,6}$]decane, thus contains hydroxymethyl groups both at positions 3 or 4 and in positions 8 or 9. It is now possible by addition of alkylene oxides, in general in quantities of 1 through 10 mol, particularly of ethylene oxide, propylene oxide, butylene oxide, etc. in the presence of basic catalysts and according to known methods to synthesize the corresponding polyether polyols. EP0023686 B1 contains more detailed preparation specifications in this connection.

The reaction of the 3(4), 8(9)-bis(hydroxymethyl)tricyclo [5.2.1.0$^{2,6}$]decanes with isocyanates to form the corresponding urethanes is likewise known. Thus DE 35 22 006 A1 describes the reaction of the 3(4), 8(9)-bis(hydroxymethyl) tricyclo[5.2.1.0$^{2,6}$]decane with 2-isocyanatoethyl methacrylate. 2-isocyanatoethyl methacrylate is commercially available or can be synthesized according to the preparation specification from DE 33 38 077 A1 by phosgenation of dihydrooxazines.

The reaction product obtained (Formula (1)) of 2-isocyanatoethyl methacrylate with 3(4), 8(9)-bis(hydroxymethyl) tricyclo[5.2.1.0$^{2,6}$]decane in a formulation following curing has a lower reaction shrinkage and a high mechanical strength.

Formula (1)

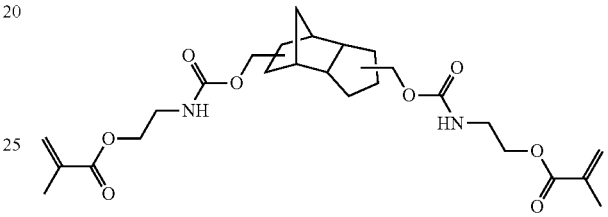

The urethane of Formula (1) still has two hydrogen atoms capable of reacting with nitrogen, which now in a second reaction stage are further reacted with excess isocyanate to form a compound to be used according to the invention. In the process the allophanate of Formula (2) initially forms as a tetrafunctionalized radically cross-linkable compound. In turn this monomer also still has hydrogen atoms capable of reacting with nitrogen, which according to the invention when reacting with further isocyanate form the hexafunctionalized, radically curable allophanate of Formula (3).

Formula (2)

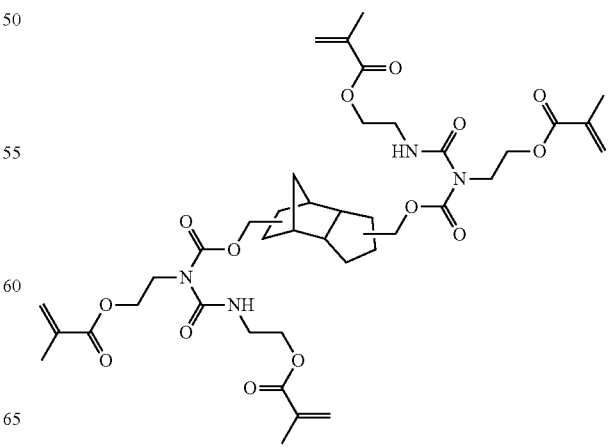

Formula (3)

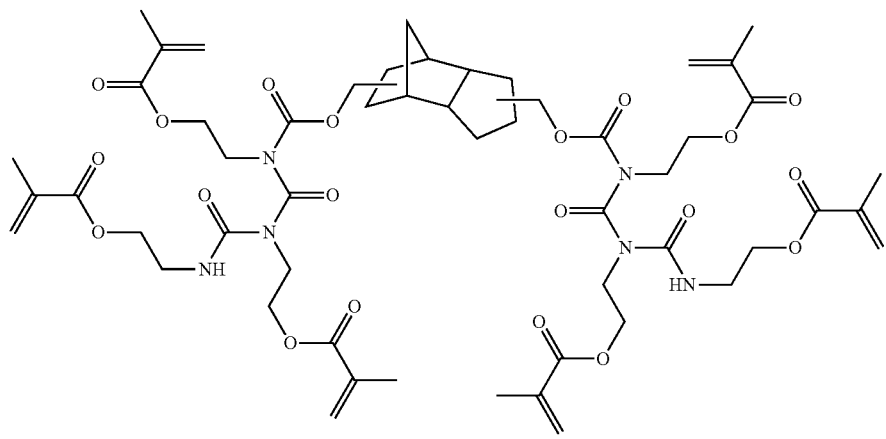

Alternatively the 3(4), 8(9)-bis(hydroxymethyl)tricyclo[5.2.1.0$^{2,6}$]decane can also be brought into a reaction with methacryloyl isocyanate. Methacryloyl isocyanate is commercially available or can be obtained by reacting methacrylamide with oxalyl chloride, as described in EP 0 143 613 B1. Through the reaction of 3(4), 8(9)-bis(hydroxymethyl)tricyclo[5.2.1.0$^{2,6}$]decane with methacryloyl isocyanate a compound of Formula (4) is obtained:

Formula (4)

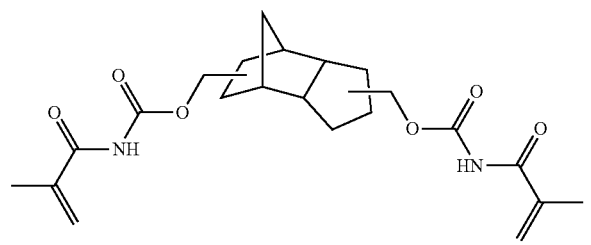

The remaining hydrogen atoms able to react with nitrogen of the compound of Formula (4) can then in turn be reacted in isocyanate reactions to form allophanates. The reaction product with 2-isocyanatoethyl methacrylate (Formula (5)) is shown here as an example.

Formula (5)

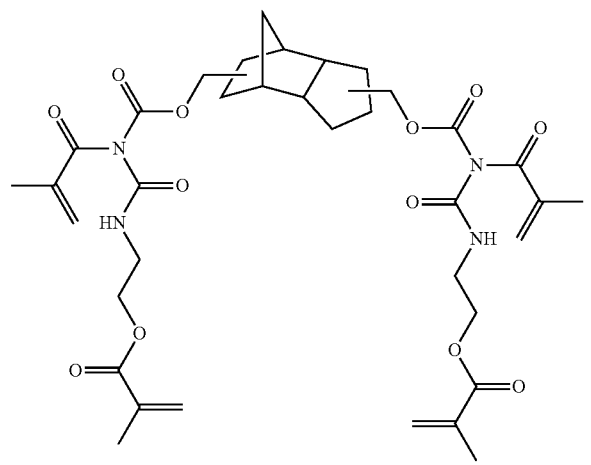

2.) Starting with 3(4), 8(9)-bis(carboxylic acid)tricyclo[5.2.1.0$^{2,6}$]decane The 3(4), 8(9)-bis(carboxylic acid)tricyclo[5.2.1.0$^{2,6}$]decane is preparable by simple oxidation of the commercially available 3(4), 8(9)-bis(formyl)tricyclo[5.2.1.0$^{2,6}$]decane. Reaction of the dicarboxylic acid with 2-isocyanatoethyl methacrylate produces the amide of Formula (8):

Formula (8)

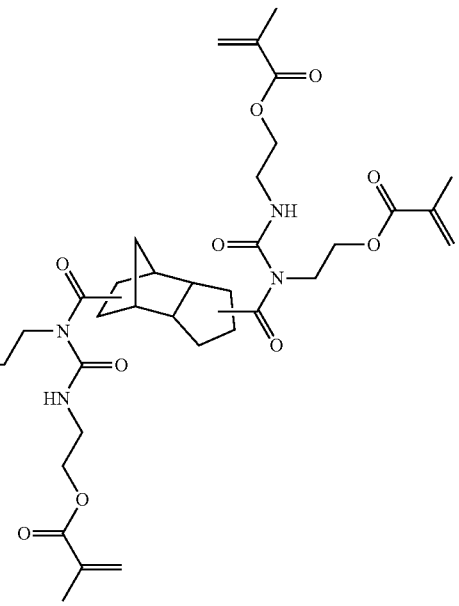

Further reaction of the two amide-hydrogen atoms of the amide of Formula (8) capable of reacting with 2-isocyanatoethyl methacrylate produces the acyl urea of Formula (9).

Formula (9)

If 3(4), 8(9)-bis(carboxylic acid)tricyclo[5.2.1.0$^{2,6}$]decane is reacted with methacryloyl isocyanate, the imide of Formula (10) results. The hydrogen atoms that react with nitrogen can here also be further reacted in isocyanate reactions.

Formula (10)

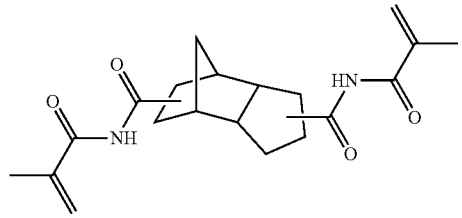

3.) Starting with 3(4), 8(9)-bis(isocyanatomethyl)tricyclo [5.2.1.0$^{2,6}$]decane The 3(4), 8(9)-bis(isocyanatomethyl)tricyclo[5.2.1.0$^{2,6}$]decane is in itself known and is one of the diisocyanate compounds commonly used in industrial applications (see DE 37 03 120 A1 and WO 2009/065873 A2). The conducting according to the invention of the second reaction stage of the isocyanate-alcohol reaction can be initiated not only starting with tricyclodecandiol and the isocyanatoethyl methacrylate, but also starting with the tricyclodecane diisocyanate and hydroxyethyl methacrylate. Through stoichiometric reaction of the two reactants the urethane of Formula (11) is obtained.

Formula (11)

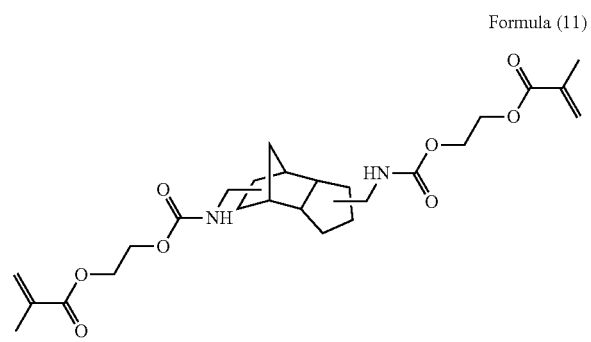

This carbamate (Formula (11)) also has two hydrogen atoms capable of reacting with nitrogen, which can be further reacted with an excess of bis(isocyanatomethyl)tricyclo [5.2.1.0$^{2,6}$]decane to form the diisocyanate of Formula (12).

Formula (12)

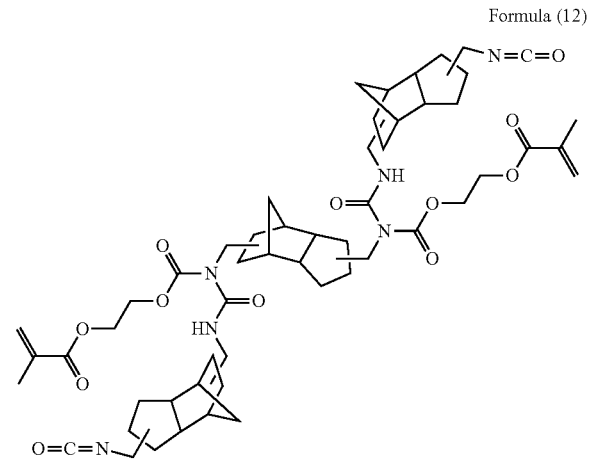

Reaction of the allophanate diisocyanate (Formula 12) with methacrylic acid produces the compound of Formula (13).

Formula (13)

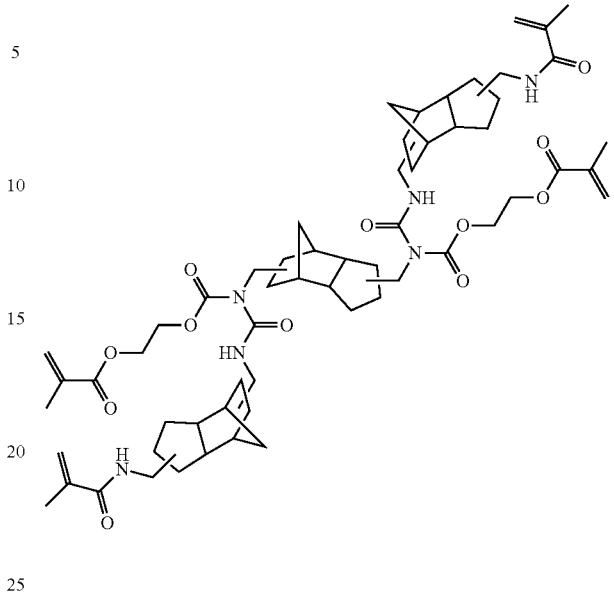

Instead of hydroxyethyl methacrylate in the reactions described by way of example above other hydroxyl compounds of (meth)acrylates can be used, wherein mixtures of acrylates and methacrylates can also be used. So—analogously to the above example—3(4), 8(9)-bis(isocyanatomethyl)tricyclo[5.2.1.0$^{2,6}$]decane can be reacted. Here, preferred hydroxyl compounds of (meth)acrylates are:

alkylene oxide mono(meth)acrylates such as for example ethylene glycol mono(meth)acrylate, diethylene glycol mono(meth)acrylate, triethylene glycol mono(meth)acrylate, tetraethylene glycol mono(meth)acrylate, etc., polyalkylene oxide mono(meth)acrylates such as for example polyethylene glycol mono(meth)acrylate, polypropylene glycol mono(meth)acrylate, polybutylene glycol mono(meth)acrylate, etc., hydroxyalkyl mono(meth)acrylates such as for example hydroxyethyl(meth)acrylate, hydroxypropyl(meth)acrylate, 2-hydroxypropyl(meth)acrylate, hydroxybutyl(meth)acrylate, 4-hydroxybutyl(meth)acrylate, hydroxypentyl(meth)acrylate, 3-hydroxy-2,2-dimethylpropyl(meth)acrylate, hydroxyhexyl(meth)acrylate, hydroxyheptyl(meth)acrylate, hydroxyoctyl(meth)acrylate, hydroxynonyl(meth)acrylate, hydroxydecyl(meth)acrylate, hydroxyundecyl(meth)acrylate, hydroxydodecyl(meth)acrylate, etc., poly(ε-caprolactone)mono(meth)acrylate, poly(γ-caprolactone)mono(meth)acrylate, etc., the mono-, di-, tetra-, or penta(meth)acrylates of polyhydric alcohols, such as glycerin, such as for example glycerin di(meth)acrylate (2-hydroxypropyl-1,3-di(meth)acrylate, 3-hydroxypropyl-1,2-di(meth)acrylate), such as trimethylolpropane, such as for example trimethylolpropane di(meth)acrylate, such as pentaerythritol, such as for example pentaerythritoltri(meth)acrylate, such as dipentaerythritol, such as for example dipentaerythritolpenta(meth)acrylate, such as ditrimethylolpropantri(meth)acrylate, such as neopentyl glycol(meth)acrylate, the (meth)acrylates of alkoxylated or phenoxylated glycerin, here preferably the (meth) acrylates of ethoxylated, propoxylated, etc. glycerin, trimethylolpropane, pentaerythritol, dipentaerythritol, ditrimethylolpropane, etc. and the technical mixtures thereof, bisphenol-A-glycidyl-(meth)acrylate (Bis-GMA), bisphenol-B-glycidyl-(meth)acrylate, bisphenol-C-glycidyl-(meth) acrylate, bisphenol-F-glycidyl-(meth)acrylate, alkoxylated bisphenol-A-glycidyl-(meth)acrylate (e.g. ethoxylated bisphenol-A-glycidyl-(meth)acrylate), etc.

All these compounds have both (meth)acrylate groups and hydroxy groups. The latter can react with isocyanate groups in the manner described above for the reaction between hydroxyethyl methacrylate and 3(4), 8(9)-bis(isocyanatomethyl)-tricyclo[5.2.1.0$^{2,6}$]decane. Thus in a single reaction step a high degree of functionalization can be achieved.

3(4), 8(9)-bis(isocyanatomethyl)tricyclo[5.2.1.0$^{2,6}$]decane can be reacted with 2-carboxylic acid-methacrylate to form the corresponding amide of Formula (16).

Formula (16)

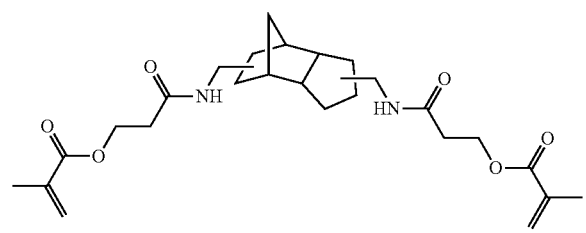

Reacting of the amide of Formula (16) with 2-isocyanatoethyl methacrylate produces the acyl urea of Formula (17).

Formula (17)

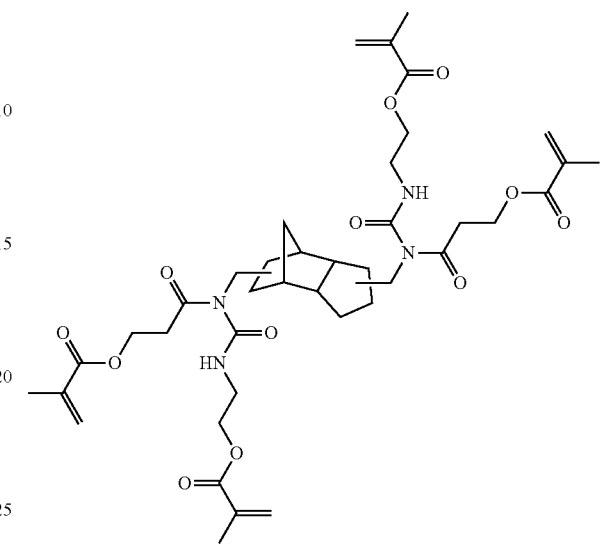

The amide of Formula (16) can also be reacted with an excess of 3(4), 8(9)-bis(isocyanatomethyl)tricyclo[5.2.1.0$^{2,6}$]decane to form the corresponding isocyanate, wherein the isocyanate so formed is further reacted with hydroxyethyl methacrylate to form the cross-linkable monomer of Formula (18).

Formula (18)

If 3(4), 8(9)-bis(isocyanatomethyl)tricyclo[5.2.1.0$^{2,6}$]decane is reacted with 2-methacryloyloxy ethyl hydrogen succinate, then the amide of Formula (19) is obtained, which is further reacted with 2-isocyanatoethyl methacrylate to form the acyl urea of Formula (20).

Further suitable carboxylic acid methacrylates can be obtained from reactions between di- or tetracarboxylic acid mono- or dianhydride with suitable OH-functionalized, curable compounds such as for example 2-hydroxyethyl methacrylate.

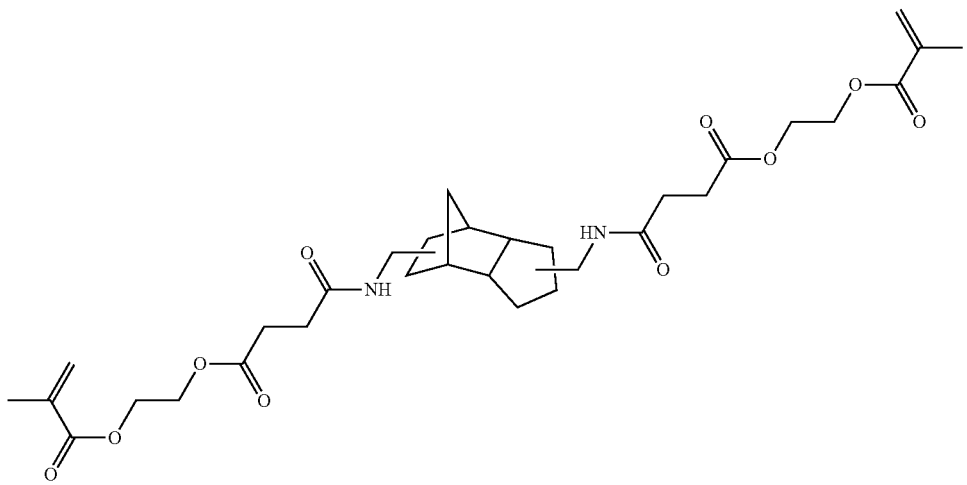

Formula (19)

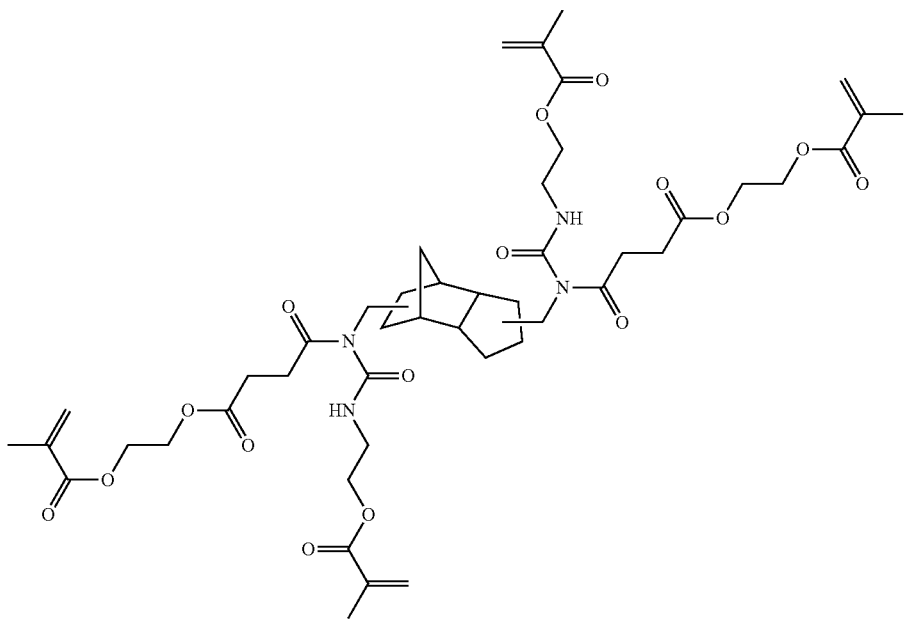

Formula (20)

4.) Starting with 3(4), 8(9)-bis(aminomethyl)tricyclo[5.2.1.0²,⁶]decane

The 3(4), 8(9)-bis(aminomethyl)tricyclo[5.2.1.0²,⁶]decane is in itself known or is preparable for example by reaction of the corresponding tosylates with ammonia. Reaction of the 3(4), 8(9)-bis(aminomethyl)tricyclo[5.2.1.0²,⁶]decane with 2-isocyanatoethyl methacrylate results in the urea compound of Formula (26) known from EP 0209700 A2.

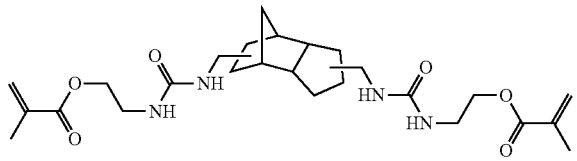

Formula (26)

Here again, there are still active hydrogen atoms capable of reacting with nitrogen which for example with an excess of isocyanate react to form the biuret of Formula (27).

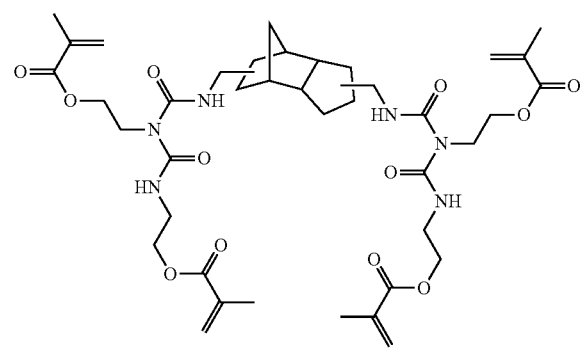

Formula (27)

The 3(4), 8(9)-bis(aminomethyl)tricyclo[5.2.1.0²,⁶]decane can also be brought into a reaction with methacryloyl isocyanate to form the corresponding acyl urea. The further reaction of the remaining hydrogen atoms reactive to nitrogen with methacryloyl isocyanate provides the biuret of Formula (28).

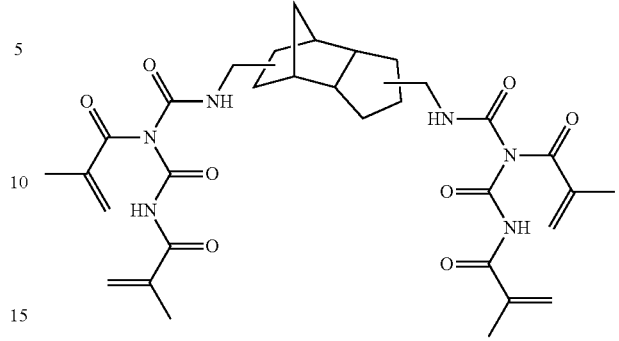

Formula (28)

By analogy to the monomers described above, which comprise a polyalicyclic structure element Q derived from the tricyclo[5.2.1.0²,⁶]decane, monomers is also preparable, which comprise a polyalicyclic structure element Q derived from a tricyclo[3.3.1.1³,⁷]decane (adamantane). The following reaction products are shown by way of examples:

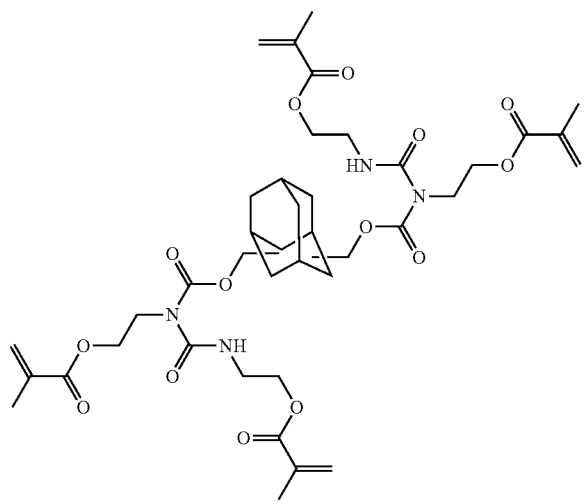

Formula (29)

The reaction of the compound of Formula (11) with diisocyanatoadamantane [(bis(isocyanatomethyl)tricyclo[3.3.1.1³,⁷]decane] provides a monomer to be used according to the invention, the molecule of which comprises two polyalicylic structure elements that differ from one another, as shown in the following graphic formula of the compound of Formula (69).

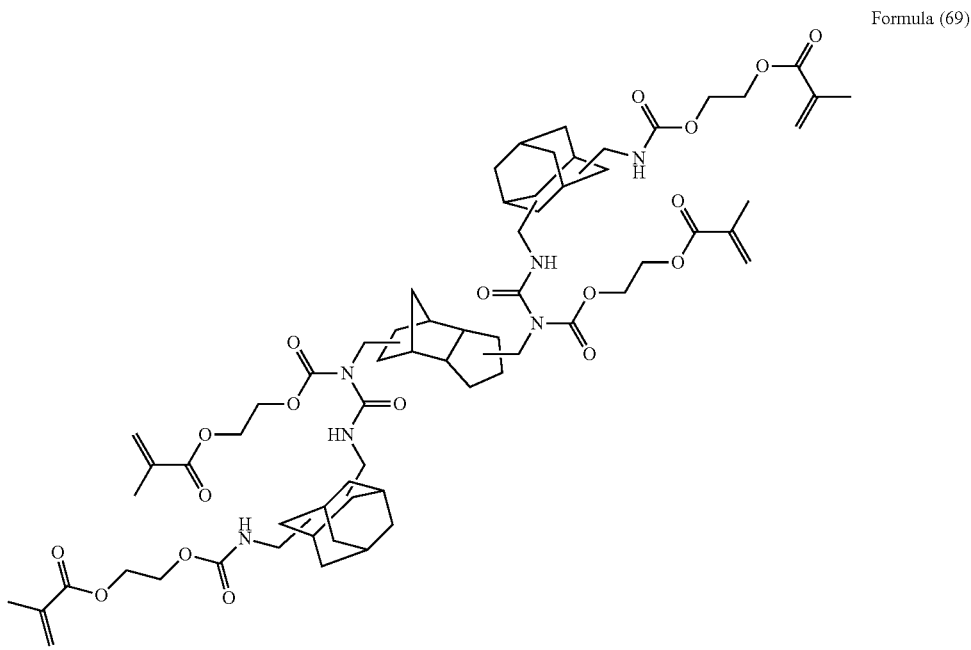

Formula (69)

Component (b2): One, Two or a Plurality of Further Radically Polymerizable Monomers from the Group Consisting of Acrylates and Methacrylates, Preferably from the Group of Methacrylates, The optional second constituent, that does not count as a monomer component (b1), of the matrix-forming monomer components is made up of radically polymerizable monomers selected from the group consisting of acrylates and methacrylates. Their function within the composite material according to the invention or to be used according to the invention is substantially to adjust the viscosity.

According to the invention methacrylic acid esters or diesters are preferred because of their high biocompatibility compared with the corresponding acrylic acid esters or diesters.

The radically polymerizable monomers of component (b2) preferably have at least two ethylenic groups.

In the patent literature a large number of diacrylate and dimethacrylate monomers are mentioned (for example also in DE 39 41 629 A1, which by way of reference is a constituent of this application, in particular the disclosure between column 6, line 15 and column 8, line 10), which are suitable for use in a composite material according to the invention or to be applied according to the invention.

In a preferred composite material according to the invention or to be used (or to be applied) according to the invention component (b2) contains one or a plurality of dimethacrylate monomers selected from the group consisting of ethylene glycol dimethacrylate (EGDMA), 1,6-hexandiol dimethacrylate (HEDMA), triethylene glycol dimethacrylate (TEDMA), 1,12-dodecandiol dimethacrylate (DODMA), ethoxylated bisphenol A dimethacrylate, polyethylene glycol dimethacrylate (PEGDMA), 7,7,9-trimethyl-4,13-dioxo-5,12-diazahexadecan-1,16-dioxydimethacrylate (UDMA), butanediol dimethacrylate, tetraethylene glycol dimethacrylate, neopentyl glycol dimethacrylate, 2-hydroxypropyl-1,3-dimethacrylate, 3-hydroxypropyl-1,2-dimethacrylate, pentaerythritol dimethacrylate, and glycerin dimethacrylate.

According to the invention preference is for a composite material, wherein the further radically polymerizable monomer(s) (b2) is (are) selected from the group consisting of triethylene glycol dimethacrylate (TEDMA) and urethane dimethacrylate (7,7,9-trimethyl-4,13-dioxo-3,14-dioxa-5, 12-diazahexadecane-1,16-dioxydimethacrylate, UDMA) and mixtures thereof. With these radically polymerizable monomers (b2) in combination with the monomers (b1), in particular with the monomers (b1) identified as preferred or particularly preferred, particularly good effects in terms of the present invention are achieved. The presence of UDMA in a composite material according to the invention or to be applied according to the invention is particularly preferred.

If as monomer component (b2) a mixture containing or consisting of triethylene glycol dimethacrylate (TEDMA) and urethane dimethacrylate (7,7,9-trimethyl-4,13-dioxo-3, 14-dioxa-5,12-diazahexadecan-1,16-dioxydimethacrylate, UDMA) is used, then the mechanical properties such as the flexural strength and in particular the modulus of elasticity are improved, while at the same time the water absorption and the surface affinity (determined by means of contact angle measurement) continue to be far below the values of a comparable material from the prior art. This is in particular the case if as the monomer component (b1) (methacrylic acid esters of the dihydroxymethyltricyclo[5.2.1.0$^{2,6}$]decane are used.

In our own research a sealing material from the prior art was used with a resin matrix composed of common dental monomers (UDMA 30%, TEDMA 37%, Bis-GMA 16% and ethoxylated Bis-GMA 17%, in each case in wt. % in relation to the mixture of monomers) and a filler mixture of glass ceramic in a total quantity of 52% (in wt. % in relation to the total composition) (see comparative example in the experimental part).

If the polymer matrix of a composite material according to the invention or to be used (to be applied) according to the invention is completely, that is to say exclusively, formed by one or a plurality of (meth)acrylic acid esters of bis(hydroxymethyl)tricyclo[5.2.1.0$^{2,6}$]decane (see Example 2, below), surprisingly both the water absorption and the contact angle with the dry tooth enamel are considerably lower than for a composite material from the prior art, wherein the mechanical properties (flexural strength and modulus of elasticity) whilst being somewhat reduced nevertheless still have acceptable values.

If the polymer matrix of a composite material according to the invention or to be used (to be applied) according to the invention is formed by (i) one or a plurality of (meth)acrylic acid esters of the bis(hydroxymethyl)tricyclo[5.2.1.0$^{2,6}$]decane and (ii) triethylene glycol dimethacrylate (TEDMA) and/or urethane dimethacrylate (7,7,9-trimethyl-4,13-dioxo-3,14-dioxa-5,12-diazahexadecane-1,16-dioxydimethacrylate, UDMA), then the mechanical properties such as flexural strength and in particular the modulus of elasticity are improved, while the water absorption and the surface affinity (indicated by the contact angle measurement) are acceptable and still well below the values of comparable materials from the prior art.

Very good results are achieved if as the monomer component (b2) a mixture of TEDMA and UDMA is used, wherein the weight ratio of TEDMA to UDMA is in the range 4:1 through 1:4, preferably in the range 3:1 through 1:3, preferably in the range 2:1 through 1:2, particularly preferably in the range 3:2 through 2:3, and quite particularly preferably in the range 4:3 through 3:4.

Particularly good results are achieved if the weight ratio of the total quantity of (meth)acrylic acid esters of the bis(hydroxymethyl)tricyclo[5.2.1.0$^{2,6}$]decane (monomer component (b1)) to the total quantity of the mixture of TEDMA and UDMA (monomer component (b2)) is in the range 4:1 through 1:3, preferably in the range 3:1 through 1:2, preferably in the range 2:1 through 2:3, particularly preferably in the range 3:2 through 2:3, and quite particularly preferably in the range 4:3 through 3:4, wherein in the monomer component (b2) in turn the above-mentioned weight ratios of TEDMA to UDMA are preferably set.

While bisphenol-A-glycidyl-methacrylate (Bis-GMA) can indeed be used, a dental composite material to be used according to the invention or applied according to the invention does not contain the compound Bis-GMA, however. Preferably a dental composite material to be used or applied according to the invention, is free from all compounds with a bisphenol-A structure element.

The racially polymerizable monomers of component (b2) which are thus not part of component (b1) can also be hydroxyl compounds. Here all hydroxyl compounds of acrylates and methacrylates normally used in dental chemistry can be used. Preference is for hydroxyl compounds of methacrylates, and here in turn preference is for 2-hydroxyethyl methacrylate, 2-hydroxypropyl methacrylate, 3-hydroxypropyl methacrylate, 1,2-dihydroxypropyl methacrylate, 1,3-dihydroxypropyl methacrylate, 2,3-dihydroxypropyl methacrylate, 2-hydroxypropyl-1,3-dimethacrylate, 3-hydroxypropyl-1,2-dimethacrylate, pentaerythritol dimethacrylate, glycerin dimethacrylate, and 2,2-bis[4-[3-methacryloyloxy-2-hydroxypropoxy]phenyl]propane.

As a further constituent photocurable acrylate or methacrylate monomers based on polysiloxanes, as for example described in DE 199 03 177 or in DE 44 16 857, which by way of reference are a constituent of this application, can also be used.

A dental composite material to be used or applied according to the invention, can further in component (b2) contain one or a plurality of acid group-containing acrylate and/or methacrylate monomers. Such acid group-containing monomers can preferably have a carboxylic acid, a phosphoric acid, a phosphonic acid, a sulfonic acid and/or a thiophosphoric acid function. The monomer can contain one or a number of acid functions in a molecule.

Suitable monomers containing a phosphoric acid group are, for example, 2-(meth)acryloyloxyethyl dihydrogen phosphate, bis[2-(meth)acryloyloxyethyl]hydrogen phosphate, 2-(meth)acryloyloxyethylphenyl hydrogen phosphate, 6-(meth)-acryloyloxyhexyl dihydrogen phosphate, 10-(meth)acryloyloxydecyl dihydrogen phosphate (MDP), 6-(meth)-acryloyloxyhexylphenyl hydrogen phosphate, 10-(meth)acryloyloxydecyl dihydrogen phosphate, 1,3-di-(meth)acryloyloxypropane-2-dihydrogen phosphate, 1,3-di-(meth)acryloyloxypropane-2-phenyl hydrogen phosphate and bis[5-(2-(meth)acryloyloxyethoxycarbonyl)heptyl]hydrogen phosphate.

Suitable monomers containing a carboxylic acid group are for example, 4-(meth)acryloxyethyl trimellith acid (4-MET), 4-(meth)acryloxyethyl trimellith acid anhydride (4-META), 4-(meth)acryloxydecyl trimellith acid, 4-(meth)acryloxydecyl trimellith acid anhydride, 11-(meth)acryloyloxy-1,1-undecane dicarboxylic acid, 1,4-di(meth)acryloyloxy pyromellith acid, 2-(meth)acryloyloxyethyl maleic acid, 2-(meth)acryloyloxyethyl phthalic acid and 2-(meth)acryloyloxyethyl hexahydrophthalic acid.

Other suitable acid group-containing monomers are mentioned in, for example, EP 0 980 682 B1 (particularly paragraphs [0059] through [0065]) or EP 0 948 955 (in particular paragraphs [0031] through [0034]), which by way of reference are a constituent of this application.

Further, phosphoric acid esters with glycerin dimethacrylate or with hydroxyethylmethacrylate or with hydroxypropylmethacrylate can also be used.

The monomers mentioned can be used individually or in mixtures.

Component (c): Initiators and/or Catalysts

Preferred composite materials to be used or applied according to the invention are photocurable and comprise photocuring initiators. Examples of a photoinitiator include substances which have solely a photo-sensitizing effect and combinations of sensitizers and accelerators.

Examples of photosensitizers are alpha-diketones, benzoin alkyl ethers, thioxanthones, benzophenones, acylphosphinoxides, acetophenones, ketals, titanocenes, sensitizing colorants, etc. The sensitizers can be used alone or in combination. Specific substance examples of the various classes can be found, for example, in DE 10 2006 019 092 A1 or in DE 39 41 629 C2, which by way of reference are a constituent of this application.

Examples of accelerators, which are used together with the sensitizers, are tertiary amines, secondary amines, barbituric acids, tin compounds, aldehydes and sulfur compounds. Specific substance examples of the various classes can be found in DE 10 2006 019 092 A1 or in DE 39 41 629 C2, which by way of reference are a constituent of this application.

Further suitable initiators and initiator combinations are described in DE 601 16 142, which by way of reference are a constituent of this application.

The photoinitiators that can be used in connection with the present invention are characterized in that through the absorption of light in the wavelength range 300 nm through 700 nm, preferably 350 nm through 600 nm and particularly preferably 380 through 500 nm, optionally in combination with one or a plurality of co-initiators, they can bring about the curing of a composite material according to the invention or to be applied according to the invention, in particular a dental composite material according to the invention or to be applied or used according to the invention.

The absorption maximum of campherquinone (CQ) is approximately 470 nm and thus in the range of blue light. Campherquinone (CQ) is one of the Pl$_2$-initiators and is regularly used together with a co-initiator.

A composite material to be applied or used according to the invention preferably contains a combination of an alpha-diketone and an aromatic tertiary amine, preferably the combination is of campherquinone (CQ) and ethyl-p-N,N-dimethylaminobenzoate (DABE)

Likewise preferred is the further combination of the "alpha-diketone/aromatic tertiary amine" system with a phosphine oxide, in particular with phenyl-bis(2,4,6-trimethylbenzoyl)phosphine oxide and/or 2,4,6-trimethylbenzoyl-diphenyl phosphine oxide. Regarding the structures of suitable phosphine oxides for use in a composite material according to the invention or to be applied or used according to the invention, reference is made to printed publications DE 38 01 511 C2, DE 10 2006 050 153 A1, EP 0 184 095 B1, DE 42 31 579 C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2, which by way of reference are a constituent of this application.

The phosphine oxides indicated in these printed publications are particularly suitable on their own or in combination with the "alpha-diketone/amine" system as a photopolymerization initiator system in a composite material according to the invention or to be used or applied according to the invention.

Alternatively borate salts, as described for example in U.S. Pat. No. 4,772,530, U.S. Pat. No. 4,954,414, U.S. Pat. No. 4,874,450, U.S. Pat. No. 5,055,372 and U.S. Pat. No. 5,057,393, can be used as photoinitiators, which by way of reference are a constituent of this application.

Further suitable photoinitiators are described in J.-P. Fouassier, Photoinitiation, Photopolymerization and Photocuring, Hanser Publishers, Munich, Vienna, New York 1995 and in J. F. Rabek (publisher), Radiation Curing in Polymer Science and Technology, Vol. II, Elsevier Applied Science, London, New York 1993, which by way of reference are a constituent of this application.

Various initiators for a chemical curing will be known to a person skilled in the art. In this connection reference is made by way of example to EP 1 720 506.

Preferred initiators for chemical curing are benzoyl peroxide, lauroyl peroxide particularly dibenzoyl peroxide in combination with amines such as N,N-dimethyl-p-toluidine, N,N-dihydroxyethyl-p-toluidine and structurally related amines.

Here the peroxides and the amines are spread across two different components of the dental material. During the mixing of the amine-containing components (so-called base paste) with the peroxide-containing components (so-called initiator or catalyst paste) through the reaction of amine and peroxide (redox reaction) the radical reaction is initiated.

Dual-curing systems comprise a combination of photoinitiators and initiators for chemical curing.

By way of example, the base paste can also contain a photoinitiator, so that the base paste can be used either on its own as a photo-curing agent or together with the initiator paste as a photo- and self-curing dental material.

Apart from the organic peroxide compounds with an oxidative effect, barbituric acids or barbituric acid derivatives and malonyl sulfamides can also be used as redox systems.

Of the barbituric acid systems the so-called Bredereck systems are of great significance. Examples of suitable Bredereck systems and references to the corresponding patent literature can be found in EP 1 839 640 and in DE 14 95 520, WO 02/092021 or in WO 02/092023, which by way of reference are a constituent of this application.

Suitable malonyl sulfamides are described in EP 0 059 451 which by way of reference is a constituent of this application. Preferred compounds here are 2,6-dimethyl-4-isobutylmalonyl sulfamide, 2,6-diisobutyl-4-propylmalonyl sulfamide, 2,6-dibutyl-4-propylmalonyl sulfamide, 2,6-dimethyl-4-ethylmalonyl sulfamide and 2.6, 6-diocytyl-4-isobutylmalonyl sulfamide.

Sulfur compounds in the oxidation stage +2 or +4 such as sodium benzene sulfinate or sodium paratoluene sulfinate can also be used.

In order to accelerate the curing the polymerization can be carried out in the presence of compounds of heavy metals such as Ce, Fe, Cu, Mn, Co, Sn or Zn, wherein copper compounds are particularly preferred. The heavy metal compounds are preferably used in the form of soluble organic compounds. Preferred copper compounds here are copper benzoate, copper acetate, copper ethyl hexanoate, copper di(methacrylate) and copper napththenate.

Component (d): Optional Further Additives

A composite material to be used or applied according to the invention in many cases comprises one or a plurality of further additives.

These additives can have various functions. Normal additives for use in dental composite materials are known to a person skilled in the art who will select the appropriate additive(s) according to the desired function. In the following examples of typical additives and their functions are provided.

Photocurable dental composite materials, as preferred according to the invention, preferably contain one or a plurality of inhibitors, also referred to as stabilizers. These are normally added in order to prevent spontaneous polymerization. They react with prematurely forming radicals, which are intercepted, prevent premature polymerization and increase the storage stability of the photocurable dental composition. Common inhibitors are phenol derivates such as hydroquinone monomethylether (HQME) or 2,6-di-tert.butyl-4-methylphenol (BHT). Further inhibitors such as tert.-butyl-hydroxy anisol (BHA), 2,2 diphenyl-1-picrylhydrazyl, galvinoxyl, triphenylmethyl radicals, 2,3,6,6,-tetramethylpiperidinyl-1-oxyl radicals (TEMPO) and derivatives of TEMPO or phenothiazine and derivatives of this compound are described in EP 0 783 880 B1 which by way of reference are a constituent of this application. Alternative inhibitors are indicated in DE 101 19 831 A1 or in EP 1 563 821 A1, which by way of reference are a constituent of this application.

A dental composite material preferred according to the invention thus comprises as an additive one or a plurality of polymerization inhibitors to increase the storage stability of the composite material, preferably selected from the group consisting of hydroquinone monomethylether (HQME), phenols, here preferably 2,6-di-tert.butyl-4-methyl phenol (BHT) and tert.-butylhydroxy anisol (BHA), 2,2-diphenyl-1-picrylhydrazyl radicals, galvinoxyl radicals, triphenylmethyl radicals, 2,3,6,6,-tetramethylpiperidinyl-1-oxyl radicals (TEMPO) and derivatives thereof and phenothiazine and derivatives thereof.

A preferred dental composite material according to the invention, that is particularly suitable for application in a therapeutic dental method as a sealing material for sealing of fissures and/or pits and/or carious lesions, comprises as an additive one or a plurality of fluoride-releasing substances, here preferably sodium fluoride and/or aminofluoride.

UV absorbers, which for example as a result of their conjugated double bonding systems and aromatic rings are capable of absorbing UV radiation, are in many cases a component of a dental composite material to be applied according to the invention. Examples of UV absorbers are 2-hydroxy-4-methoxybenzophenone, salicylic acid phenyl ester, 3-(2'-hydroxy-5'-methylphenyl)-benzotriazole, or diethyl-2,5-dihydroxy-terephthalate.

Since the teeth are to be rebuilt to look as true to life as possible, it is necessary for the dental composite materials to be applied according to the invention to be provided in the most varied of color tones. To this end as a rule inorganic colorants and organic pigments in very small quantities are used, which in preferred configurations are thus used as an additive.

Further optional additives are aromatic substances.

Preferred composite materials according to the invention or to be applied according to the invention are those which comprise the components identified above as preferred. Here a number of combinations are advantageous. Particular preference is for novel composite materials which in or as component (b1) comprise preferred compounds of the structure $Q(Y_xZ_e)_b$ with x=1 discussed above.

Preference is thus for a composite material consisting of or comprising:
(a) as the filler component a total quantity of fillers in the range 0.5 through 60 wt. %, in relation to the total weight of the composite material wherein the total quantity of fillers is a mixture of fillers comprising
  (a1) a total quantity in the range 0.5 through 60 wt. % of non-agglomerated, organically surface-modified nanoparticles with an average particle size of less than 200 nm (preferably less than 60 nm) and
  (a2) a total quantity in the range 0 through 59.5 wt. % of microparticles with an average particle size in the range 0.4 μm through 10 μm, and
  (a3) optionally further fillers,
  wherein the weight percentages given for components (a1) and (a2) in each case relate to the total weight of the composite material,
(b) as the monomer component a total quantity of polymerizable monomers in the range 39 through 98.5 wt. %, in relation to the total weight of the composite material, wherein the total quantity of polymerizable monomers comprises
  (b1) one, two or a plurality of monomers selected from the group consisting of compounds (monomers) with the structure $Q(Y_xZ_e)_b$, wherein the following applies:
    Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ are substituted by alkyl groups (here preferably C1-C4-alkyl), alkoxy groups (here preferably C1-C4-alkoxy), halogen atoms (here preferably F) or trifluormethyl groups;
    b is an integer selected from the group of integers 1, 2, 3 and 4,
    each Z represents a structure element, which independently of any other structure elements Z is selected from the group consisting of

—O—(C=O)—CH=CH$_2$, —O—(C=O)—C(CH$_3$)=CH$_2$,

—(C=O)—CH=CH$_2$, —(C=O)—(CH$_3$)=CH$_2$

—CH=CH$_2$, —C(CH$_3$)=CH$_2$ and —O—CH=CH$_2$, each index e is an integer, which independently of any other indices e is selected from the group of integers 1, 2, 3 and 4,
    each index x independently of any other indices x represents 0 or 1,
    each Y in the structure $Q(Y_xZ_e)_b$ where x=1 represents a structure element, which binds the polyalicyclic structure element Q with e structure elements Z, wherein each Y is selected independently of any other structure elements Y,
  (b2) optionally one, two or a plurality of further radically polymerizable monomers from the group consisting of acrylates and methacrylates, preferably from the group of methacrylates, wherein the further radically polymerizable monomer(s) are not compounds (monomers) of the structure $Q(Y_xZ_e)_b$ defined above,
(c) one or a plurality of initiators and/or catalysts, preferably in a quantity of up to 1 wt. %, in relation to the total weight of the composite material, and
(d) optionally one or a plurality of additives
for application in a therapeutic dental method as a sealing material for sealing of fissures and/or pits and/or carious lesions
wherein the, one, two or a plurality of the monomers of component (b1) is or are selected from the group consisting of compounds (monomers) of structure $Q(Y_xZ_e)_b$ with x=1 with one, two, three, four or a plurality of functional groups, selected from the group consisting of N-acyl urea, allophanate and biuret,
wherein the following applies:
  Q represents a saturated or olefinically unsaturated polyalicyclic structure element selected from the group consisting of bicyclic, tricyclic, tetracyclic, pentacyclic and hexacyclic hydrocarbon radicals, wherein none, one, two or a plurality of the hydrogen atoms of this polyalicyclic structure element 0 not substituted by substituents $YZ_e$ is or are substituted by alkyl groups, alkoxy groups, halogen atoms or trifluormethyl groups;
  b is an integer selected from the group of integers 2, 3, 4;
  each Z represents a structure element, which independently of any other structure elements Z is selected from the group consisting of

—O—(C=O)—CH=CH$_2$, —O—(C=O)—C(CH$_3$)=CH$_2$,

—(C=O)—CH=CH$_2$, —(C=O)—C(CH$_3$)=CH$_2$,

—CH=CH$_2$, —C(CH$_3$)=CH$_2$ and —O—CH=CH$_2$, each index e is an integer, which independently of any other indices e is selected from the group of integers 1, 2, 3 and 4;
  each Y represents a structure element that in the structure $Q(Y_xZ_e)_b$ with x=1 links the polyalicyclic structure element Q with e structure elements Z and contains or consists of a structure element selected from the group consisting of

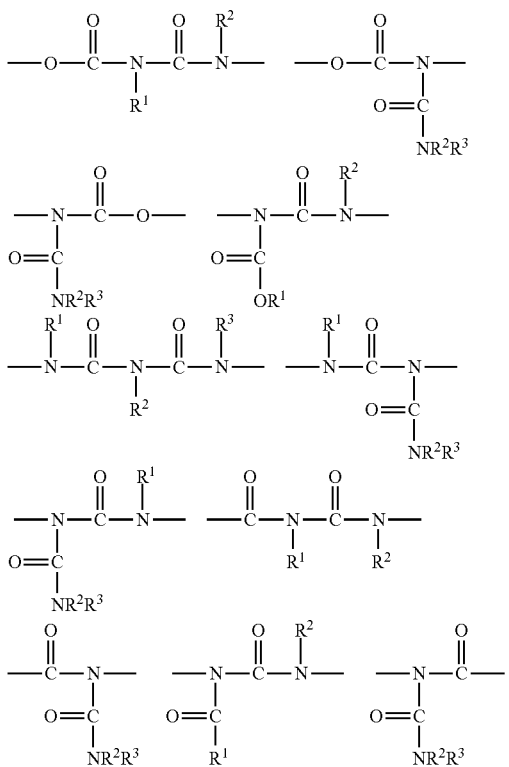

wherein $R^1$, $R^2$, and $R^3$ represent other radicals of the compound, wherein in each case the bond arranged to the left of the graphic formula is closer to the structure element Q and the bond arranged on the right is closer to the structure element Z.

Regarding the preferred configurations of such preferred composite materials the above statements on preferred components apply.

The present invention also relates to a method for treatment or for prevention of a dental condition, characterized in that a composite material to be applied according to the invention, preferably in one of the configurations identified as preferred, is used as a sealing material for sealing of fissures and/or pits and/or carious lesions.

EXEMPLARY EMBODIMENTS

The invention is further explained using the following examples. Unless otherwise indicated all data relate to the weight.
Abbreviations and Materials Used
TEDMA=triethylene glycol dimethacrylate
UDMA=7,7,9-trimethyl-4,13-dioxo-5,12-diazahexadecane-1,16-dioxydimethacrylate
DABE=N,N-dimethyl-p-aminobenzoic acid
CQ=campherquinone
BHT=2,6-di-tert.butyl-4-methyl phenol (stabilizer)
Preparation of Composite Materials Composite materials to be used or applied according to the invention as well as a comparative material not according to the invention, respectively, were prepared as follows:

The monomer (b1) and optionally the monomer(s) (b2), initiators (c) and additives (d) are initially homogenized in a plastic container using a KPG stirrer. Then the filler(s) of component (a) is (are) added and through the thorough mixing of these with a dual-planet mixer a homogenous paste prepared. Optionally, further homogenization can be performed on a three-cylinder mill.

Measurement Methods:

Determination of the Abrasion (ACTA)

The three-media Acta Abrasion was determined according to the J. Dent. Suppl. 1, 1994, 22, 21-27 after 200,000 cycles.

Flexural Strength

The flexural strength was determined analogous to ISO 4049. For this purpose the respective material to be investigated was filled free from air bubbles in suitable Teflon moulds, and then covered with film and glass plate and the excesses pressed out by means of a screw clamp. The test specimens were cured for 24 hours at 37° C. in the water bath.

The size of the test specimen (2 mm×2 mm) was measured in the centre with a measuring accuracy of 0.01 mm. Then the test specimens were stressed in a Zwick Z005 universal testing machine (Zwick GmbH, Ulm, Deutschland) at a feed rate of 0.75 mm/min until rupture.

Surface Affinity: Contact Angle with Dry Tooth Enamel

The surface affinity was determined by measuring the contact angle with the dry tooth enamel.

For the contact angle measurements (KW, in degrees [°]) on dry tooth enamel an extracted human molar was used. Prior to measurement this was dried by wiping with a tissue. Then a drop of the material to be investigated was applied to the enamel area of the tooth. The contact angle was then measured over a period of 30 seconds with a contact angle measuring instrument (DSA 100 from Krüss).

Water Absorption

The water absorption was determined analogous to ISO 4049. For this purpose the respective composite materials were filled free from air bubbles in appropriate Teflon moulds, and then covered with film and glass plate and the excesses pressed out by means of a screw clamp. The test specimens with a diameter of 15.0±0.1 mm and a height of 1.0±0.1 mm were photocured in segments. Then the test specimens were stored in a desiccator at 37° C. After 22 hours the test specimens were removed, placed in a second desiccator at 23° C. for 2 hours and then weighed to an accuracy of 0.1 mg. This cycle was repeated until a constant weight $m_1$, had been achieved.

Following complete drying two measurements of the diameter were taken at right angles to each other with a measuring accuracy of 0.01 mm and from these the average diameter was calculated. The thickness of the test specimen was measured at the centre and at four evenly spaced points on the circumference to an accuracy of 0.01 mm. The average diameter and the average thickness were used to calculate the volume V.

Then the test specimens were stored for 7 days in water at 37° C., after which they were removed, rinsed with water and dabbed off until no further moisture could be seen on the surface. The test specimens were waved back and forth for 15 seconds in the air and 1 minute after removal from the water they were weighed. The weight is given as $m_2$.

Then the test specimens were again stored in a desiccator at 37° C. After 22 hours the test specimens were removed, placed in a second desiccator at 23° C. and then weighed to an accuracy of 0.1 mg. This cycle was repeated until a constant weight $m_3$, had been achieved.

The water absorption, $W_{sp}$, was calculated according to the following equation:

$$W_{sp} = \frac{m_2 - m_3}{V}$$

Where:

$m_2$ is the weight of the test specimen following storage in water for 7 days in μg;

$m_3$ is the weight of the re-dried test specimen in μg;

V is the volume of the test specimen in mm³.

Viscosity

The viscosity was determined using a Physica MCR 301 rheometer (Anton Paar GmbH, Graz, Austria). To this end the material under investigation was placed on the measuring plate of a plate-plate system (D=25 mm, gap=1 mm) and the viscosity determined at 23° C. and a shear rate of 10/s.

With the (slianized) nanofiller that was then used it was a case of slianized silica particles with an average particle size of 40 nm.

Further definitions:

With the "TCD monomer" compound that was then used it was a case of bis(methacrylolyoxymethyl)-tricyclo [5.2.1.0$^{2,6}$]decane.

The filler used in the following, "pyrogenic silica (organically surface-modified)" is a hydrophobic silica with a BET surface (according to DIN EN ISO 9277) of 150 m²/g, a tamped density (according to DIN EN ISO 787-11) of approximately 200 g/l and a (presumed) primary particle size of 12 nm. The surface of the silica is provided with —OSi(CH$_3$)$_3$-groups.

TABLE 1

| Example | 1 | 2 | 3 | 4 | Comparison |
|---|---|---|---|---|---|
| TCD monomer | 0.00 | 47.12 | 31.56 | 15.72 | 0.00 |
| Monomer of Formula (2) | 21.38 | 0.00 | 0.00 | 0.00 | 0.00 |
| UDMA | 17.35 | 0.00 | 0.00 | 7.07 | 14.14 |
| TEDMA | 12.44 | 0.00 | 0.00 | 8.71 | 17.43 |
| Bis-GMA | 0.00 | 0.00 | 7.54 | 7.55 | 7.54 |
| Ethoxylated Bis-GMA | 0.00 | 0.00 | 8.02 | 8.07 | 8.01 |
| UV stabilizer | 0.25 | 0.24 | 0.24 | 0.24 | 0.24 |
| DABE | 0.22 | 0.21 | 0.21 | 0.21 | 0.21 |
| Catalyst (CQ) | 0.15 | 0.14 | 0.14 | 0.14 | 0.14 |
| BHT | 0.09 | 0.09 | 0.09 | 0.09 | 0.09 |
| Glass ceramic 0.7 μm (silanized) | 26.85 | 45.94 | 45.94 | 45.94 | 45.94 |
| Reactive aluminum silicate glass (<10 μm) | 4.13 | 4.07 | 4.07 | 4.07 | 4.07 |
| Pyrogenic silica (organically surface-modified) | 1.65 | 1.59 | 1.59 | 1.59 | 1.59 |
| Titanium dioxide (silanized) | 0.62 | 0.60 | 0.60 | 0.60 | 0.60 |
| Nanofiller (silanized) | 14.87 | 0.00 | 0.00 | 0.00 | 0.00 |
| Flexural strength [MPa] | 138 | 109 | 126 | 128 | 104 |
| Modulus of elasticity [MPa] | 6319 | 3684 | 4603 | 4675 | 4446 |
| KW [°] dry enamel | 29.5 | 29.0 | 51.90 | 45.10 | 67.1 |
| Water absorption [μg/mm³] | 11.91 | 5.12 | | | 25.14 |
| Viscosity [Pas] | | 3.00 | 8.30 | 4.60 | 2.80 |
| Acta abrasion | 75 μm | | | | 145 μm |
| Total fillers | 48.12 | 52.20 | 52.20 | 52.20 | 52.20 |

TABLE 2

| | Example | | | | | |
|---|---|---|---|---|---|---|
| | 5 | 6 | 7 | 8 | 9 | 10 |
| TCD monomer | 23.64 | 28.37 | 18.91 | 21.38 | 17.91 | 21.38 |
| UDMA | 11.82 | 11.82 | 14.19 | 17.35 | 12.31 | 16.91 |
| TEDMA | 11.47 | 6.74 | 13.83 | 12.44 | 10.44 | 13.75 |
| UV stabilizer | 0.24 | 0.24 | 0.24 | 0.25 | 0.25 | 0.25 |
| DABE | 0.21 | 0.21 | 0.21 | 0.22 | 0.22 | 0.22 |
| Catalyst (CQ) | 0.14 | 0.14 | 0.14 | 0.15 | 0.15 | 0.15 |
| BHT | 0.09 | 0.09 | 0.09 | 0.09 | 0.09 | 0.09 |
| Glass ceramic 0.7 μm (silanized) | 46.11 | 46.11 | 46.11 | 26.85 | 27.15 | 0.00 |
| Reactive aluminum silicate glass (<10 μm) | 4.08 | 4.08 | 4.08 | 4.13 | 4.13 | 0.00 |
| Pyrogenic silica (organically surface-modified) | 1.60 | 1.60 | 1.60 | 1.65 | 1.65 | 0.00 |
| Titanium dioxide (silanized) | 0.60 | 0.60 | 0.60 | 0.62 | 0.62 | 0.00 |
| Nanofiller (silanized) | 0.00 | 0.00 | 0.00 | 14.87 | 25.08 | 47.25 |
| Flexural strength [MPa] | 137 | 127 | 130 | 135 | 131 | |
| Modulus of elasticity [MPa] | 6106 | 6070 | 5334 | 6214 | 6279 | |
| KW [°] dry enamel | 29.3 | 46.7 | 30.4 | 31.5 | 36.3 | 33.7 |
| Water absorption [μg/mm³] | 7.61 | 6.53 | 11.72 | 13.45 | 12.61 | 12.89 |
| Acta abrasion | | | | | | 62 μm |
| Total fillers | 52.39 | 52.39 | 52.39 | 48.12 | 58.63 | 47.25 |

Synthesis of the Compound of Formula (2)

0.95 g (4.84 mmol) of 3(4), 8(9)-bis(hydroxymethyl)tricyclo[5.2.1.0$^{2,6}$]decane were dissolved in 10 ml of toluene and 0.04 g of BHT and 0.103 g of the catalyst solution were added. Under agitation 3.00 g (19.34 mmol, 4 equivalents) of isocyanatoethyl methacrylate dissolved in 10 ml of toluene were droppered in. Once addition was complete the dropping funnel was replaced by a reflux condenser and the reaction mixture heated to 120° C. with the continuation of the reaction being monitored by IR spectroscopy. After 72 hours a further 0.102 g of catalyst solution was added and heating continued until no further isocyanate bands were detected. The solvent was removed using the rotary evaporator. The allophanate of formula (2) was obtained in a yield of 3.83 g (4.69 mmol, 97%) as a light yellowy oil.

Examples 2 through 10 were repeated exchanging the TCD monomers used there for the compound of formula (2); these further examples are referred to as Examples S2 through S10. All parameters determined in Examples 2 through 10 were also determined for Examples S2 through S10. The values of the parameters determined for Examples S2 through S10 are similar to those from Examples 2 through 10 and to some extent surpass these. This shows that in addition to Example 1 according to the invention, the compound of Formula (2), which is representative of the compounds according to the invention, is eminently suitable for use in composite materials according to the invention.

The invention claimed is:

1. A composite material comprising:
(a) as the filler component a total quantity of fillers in the range 0.5 through 60 wt. %, in relation to the total weight of the composite material wherein the total quantity of fillers is a mixture of fillers comprising
(a1) a total quantity in the range 0.5 through 60 wt. % of non-agglomerated, organically surface-modified nanoparticles with an average particle size of less than 200 nm and
(a2) a total quantity in the range 0 through 55 wt. % of microparticles with an average particle size in the range 0.4 μm through 10 μm, and
(a3) optionally additional fillers,
wherein the weight percentages given for components (a1) and (a2) in each case relate to the total weight of the composite material,
(b) as the monomer component a total quantity of polymerizable monomers in the range 24 through 98.5 wt. %, in relation to the total weight of the composite material, wherein the total quantity of polymerizable monomers comprises
(b1) one, two or a plurality of monomers selected from the group consisting of monomers with the structure $Q(Y_xZ_e)_b$, wherein the following applies:
Q represents a saturated or olefinically unsaturated polyalicyclic structure element selected from the group consisting of bicyclic, tricyclic, tetracyclic, pentacyclic and hexacyclic hydrocarbon radicals, wherein optionally one, two or a plurality of the hydrogen atoms of this polyalicyclic structure element Q not substituted by substituents $Y_xZ_e$ is or are substituted by alkyl groups, alkoxy groups, halogen atoms or trifluormethyl groups;
b is an integer selected from the group of integers 1, 2, 3 and 4,
each Z represents a structure element, which independently of any other structure elements Z is selected from the group consisting of

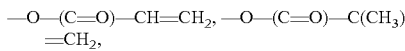

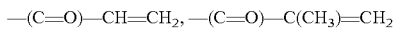

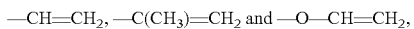

each index e is an integer, which independently of any other indices e is selected from the group of integers 1, 2, 3 and 4,
each index x independently of any other indices x represents 0 or 1,
each Y in the structure $Q(Y_xZ_e)_b$ where x=1 represents a structure element, which binds the polyalicyclic structure element Q with e structure elements Z, wherein each Y is selected independently of any other structure elements Y,
(b2) optionally one, two or a plurality of additional radically polymerizable monomers from the group consisting of acrylates and methacrylates, wherein the further radically polymerizable monomer(s) are not compounds (monomers) of the structure $Q(Y_xZ_e)_b$ defined above,
(c) one or a plurality of initiators and/or catalysts, and
(d) additionally optionally one or a plurality of other additives.

2. The composite material for application as claimed in claim 1, wherein said one or a plurality of initiators and/or catalysts of component (c) is present in an amount of up to 1 wt. %, in relation to the total weight of the composite material.

3. The composite material for application as claimed in claim 1, wherein the filler component (a) comprises
(a1) a total quantity in the range 0.5 through 59.5 wt. % of non-agglomerated, organically surface-modified nanoparticles with an average particle size of less than 60 nm and/or
(a2) a total quantity in the range 0.5 through 55 wt. % of microparticles with an average particle size in the range 0.4 μm through 10 μm, and
(a3) optionally additional fillers,
wherein the weight percentages given for components (a1) and (a2) in each case relate to the total weight of the composite material.

4. The composite material for application as claimed in claim 1, wherein the filler component (a) further comprises
(a3) a total quantity in the range 0 through 15 wt. % of additional fillers,
wherein the weight percentage given for component (a3) relates to the total weight of the composite material.

5. The composite material for application as claimed in claim 1, wherein the monomer component (b) contains
(b1) one, two or a plurality of radically polymerizable monomers of structure $Q(Y_xZ_e)_b$ as defined in claim 1 and
(b2) one, two or a plurality of additional radically polymerizable monomers from the group consisting of acrylates and methacrylates, wherein the further radically polymerizable monomer(s) are not compounds (monomers) of the structure $Q(Y_xZ_e)_b$ as defined in claim 1,
wherein the ratio of the total weight of component (b1) to the total weight of component (b2) is in the range 4:1 through 1:3.

6. The composite material for application as claimed in claim 5, wherein the ratio of the total weight of component (b1) to the total weight of component (b2) is in the range 3:1 through 1:2.

7. The composite material for application as claimed in claim 1, wherein the structure element Q of the compounds of structure $Q(Y_xZ_e)_b$ of component (b1) represents a tricyclo[5.2.1.0$^{2,6}$]decane radical, a tricyclo[5.2.1.0$^{2,6}$]dec-3-ene radical, a tricyclo[3.3.1.1$^{3,7}$]decane radical or a bicyclo[2.2.1]heptane radical.

8. The composite material for application as claimed in claim 1, wherein one, two or a plurality of compounds of structure $Q(Y_xZ_e)_b$, have a tricyclo[5.2.1.0$^{2,6}$]-decane or tricyclo[5.2.1.0$^{2,6}$]-decene structure element and Z is selected from the group consisting of —O—(C=O)—CH=CH$_2$ and —O—(C=O)—C(CH$_3$)=CH$_2$.

9. The composite material for application as claimed in claim 1, wherein one, two or a plurality of compounds of structure $Q(Y_xZ_e)_b$, have a tricyclo[5.2.1.0$^{2,6}$]-decane or tricyclo[5.2.1.0$^{2,6}$]-decene structure element and Z is —O—(C=O)—C(CH$_3$)=CH$_2$.

10. The composite material for application as claimed in claim 1, wherein component (b1) comprises of bis(methacryloyloxymethyl)tricyclo[5.2.1.0$^{2,6}$]decane and/or bis(acryloyloxymethyl)tricyclo[5.2.1.0$^{2,6}$]decane.

11. The composite material for application as claimed in claim 1, wherein the monomer component (b2) comprises monomers selected from the group consisting of triethylene glycol dimethacrylate (TEDMA) and urethane dimethacrylate (7,7,9-trimethyl-4,13-dioxo-3,14-dioxa-5,12-diazahexadecane-1,16-dioxydimethacrylate, UDMA) and mixtures thereof.

12. The composite material for application as claimed in claim 1, wherein the composite material does not contain any bisphenol-A-glycidyl-(meth)acrylate (Bis-GMA).

13. The composite material for application as claimed in claim 1, wherein the composite material does not contain any compound with a bisphenol-A structure element.

14. The composite material for application as claimed in claim 1, wherein at least part of the microparticles of component (a2) are organically surface-modified particles, and/or
  at least part of the microparticles of component (a2) are dental glass particles,
    wherein part of the microparticles of component (a2) are organically surface-modified dental glass particles.

15. The composite material for application as claimed in claim 1, wherein at least part of the microparticles of component (a2) are organically surface-modified silanized particles, and/or at least part of the microparticles of component (a2) are dental glass particles,
    wherein part of the microparticles of component (a2) are organically surface-modified silanized dental glass particles.

16. The composite material for application as claimed in claim 1, wherein component (a1) comprises non-agglomerated, organically surface-modified nanoparticles selected from the group consisting of oxides and mixed oxides, selected from the oxides or mixed oxides of the elements silicon, titanium, yttrium, strontium, barium, zirconium, hafnium, niobium, tantalum, tungsten, bismuth, molybdenum, tin, zinc, ytterbium, lanthanum, cerium, aluminum and mixtures thereof.

17. The composite material for application as claimed in claim 1, wherein the tiller mixture (a) consists of (a1) non-agglomerated, organically surface-modified nanoparticles with an average particle size of less than 200 nm.

18. The composite material for application as claimed in claim 1, wherein the contact angle of the composite material with dry tooth enamel, measured with a contact angle measuring instrument from Krüss (DSA 100), is less than 60°.

19. The composite material for application as claimed in claim 1, wherein the contact angle of the composite material with dry tooth enamel, measured with a contact angle measuring instrument from Krüss (DSA 100), is less than 50°.

20. The composite material as claimed in claim 1, wherein the water absorption of the composite material is less than 15 µg/mm$^3$.

21. The composite material as claimed in claim 1, wherein the water absorption of the composite material is less than 13 µg/mm$^3$.

22. The composite material for application as claimed in claim 1, comprising a component (a2), having
  one or a plurality of first microparticle fractions, which in each case have an average particle size in the range 1 µm through 10 µm,
  and
  one or a plurality of second microparticle fractions, which in each case have an average particle size in the range >0.4 µm through <1 µm.

23. The composite material as claimed in claim 1, wherein the monomer component (b) is present in a total quantity in the range 44 through 98.5 wt. %, in relation to the total weight of the composite material.

* * * * *